(12) United States Patent
Li et al.

(10) Patent No.: US 9,272,992 B2
(45) Date of Patent: Mar. 1, 2016

(54) (1S,2S,3S,4R)-3-[(1S)-1-ACETYLAMINO-2-ETHYL-BUTYL]-4-GUANIDINO-2-HYDROXY-CYCLOPENTYL-L-CARBOXYLIC ACID HYDRATES PHARMACEUTICAL USES THEREOF

(71) Applicant: Institute of Pharmacology and Toxicology Academy of Military Medical Sciences P.L.A., China, Beijing (CN)

(72) Inventors: Song Li, Beijing (CN); Wu Zhong, Beijing (CN); Zhibing Zheng, Beijing (CN); Xinbo Zhou, Beijing (CN); Junhai Xiao, Beijing (CN); Yunde Xie, Beijing (CN); Lili Wang, Beijing (CN); Xingzhou Li, Beijing (CN); Guoming Zhao, Beijing (CN); Xiaokui Wang, Beijing (CN); Hongying Liu, Beijing (CN)

(73) Assignee: Institute of Pharmacology and Toxicology Academy of Military Medical Sciences P.L.A., China, Beijing (CN)

(*) Notice: Subject to any disclaimer, the term of this patent is extended or adjusted under 35 U.S.C. 154(b) by 167 days.

(21) Appl. No.: 13/968,645

(22) Filed: Aug. 16, 2013

(65) Prior Publication Data
US 2013/0331604 A1 Dec. 12, 2013

Related U.S. Application Data

(62) Division of application No. 12/673,355, filed as application No. PCT/CN2008/001459 on Aug. 13, 2008, now abandoned.

(30) Foreign Application Priority Data

Aug. 14, 2007 (CN) .......................... 2007 1 0143607

(51) Int. Cl.
| | | |
|---|---|---|
| A61K 31/24 | (2006.01) | |
| A01N 37/12 | (2006.01) | |
| A01N 37/44 | (2006.01) | |
| C07C 279/16 | (2006.01) | |
| C07C 277/06 | (2006.01) | |
| C07C 277/08 | (2006.01) | |

(52) U.S. Cl.
CPC .............. *C07C 279/16* (2013.01); *C07C 277/06* (2013.01); *C07C 277/08* (2013.01); *C07B 2200/07* (2013.01); *C07C 2101/08* (2013.01)

(58) Field of Classification Search
CPC .............. C07C 277/08; C07C 2101/08; C07B 2200/07
USPC .......................................................... 514/563
See application file for complete search history.

(56) References Cited

U.S. PATENT DOCUMENTS 7,208,176 B2 4/2007 Faour et al.

FOREIGN PATENT DOCUMENTS

| CN | 1986521 A | 6/2007 |
|---|---|---|
| EP | 1 970 061 A1 | 9/2008 |
| JP | 2006-512906 | 4/2006 |
| WO | WO 9933781 A1 | 7/1999 |
| WO | WO 01/00571 A1 | 1/2001 |
| WO | WO 2004/028471 A2 | 4/2004 |
| WO | WO 2007/075102 A1 | 7/2007 |
| WO | WO 2007087056 A2 | 8/2007 |

OTHER PUBLICATIONS

Bantia. "Anti-influenza virus activity of peramivir in mice with single intramuscular injection," Antiviral Research 69, 2006, pp. 39-45.
BioCryst Pharmaceuticals. A Study to Evaluate the Efficacy and Safety of Intravenous Peramivir in Subjects with Uncomplicated Influenza. In: ClinicalTrials.gov [Internet]. United States Food and Drug Administration. 2012—Dec. 11, 2012. NLM Identifier: NCT01224795.
BioCryst Pharmaceuticals. Intramuscular Peramivir in Subjects with Uncomplicated Acute Influenza. In: ClinicalTrials.gov [Internet]. United States: Food and Drug Administration. 2012—Dec. 11, 2012. NLM Identifier: NCT00610935.
Keller, Egbert et al.; "Zeitschrift fuer Naturforschung"; *Chemical Sciences*; 2007, vol. 62, No. 8, pp. 983-987.
Kohno, S., Yen, M., Cheong, H., Hirotsu, N., Ishida, T., Kadota, J., Mizuguchi, M., Kida, H., and Shimada, J. (Nov. 2011). Phase III Randomized, Double-Blind Study Comparing Single-Dose Intravenous Peramivir with Oral Oseltamivir in Patients with Seasonal Influenza Virus Infection. *Antimicrobial Agents and Chemotherapy*, vol. 55, No. 11, p. 5267-5276.
Sidwell. "Influence of virus strain, challenge dose, and time of therapy initiation on the in vivo influenza inhibitory effects of RWJ-270201," Antiviral Research 51, 2001, pp. 179-187.
Written Opinion of the International Searching Authority, International Application No. PCT/CN2008/001459 (Oct. 23, 2008).

*Primary Examiner* — San-Ming Hui
(74) *Attorney, Agent, or Firm* — Brinks Gilson & Lione

(57) ABSTRACT

The present invention relates to (1S,2S,3S,4R)-3-[(1S)-1-acetylamino-2-ethyl-butyl]-4-guanidino-2-hydroxy-cyclopentyl-1-carboxylic acid hydrates compounds, preparing methods thereof, pharmaceutical compositions containing said compounds and preparing methods thereof, and the clinical uses of said compounds as neuramidinase inhibitors for anti-influenza.

20 Claims, No Drawings

(1S,2S,3S,4R)-3-[(1S)-1-ACETYLAMINO-2-ETHYL-BUTYL]-4-GUANIDINO-2-HYDROXY-CYCLOPENTYL-L-CARBOXYLIC ACID HYDRATES PHARMACEUTICAL USES THEREOF

CROSS-REFERENCE TO RELATED APPLICATIONS

This application is a division of U.S. patent application Ser. No. 12/673,355, which was the U.S national stage of PCT International Patent Application No. PCT/CN2008/001459, filed Aug. 13, 2008, each of which is incorporated by reference in its entirety.

TECHNICAL FIELD

The present invention relates to (1S,2S,3S,4R)-3-[(1S)-1-acetylamino-2-ethyl-butyl]-4-guanidino-2-hydroxy-cyclopentyl-1-carboxylic acid hydrates compounds, preparing methods thereof, pharmaceutical compositions comprising said compounds and use of the same for anti-influenza.

BACKGROUND ART

Suddenly occurring new-type viral infectious disease is a type of highly infectious and harmful disease resulted from self-evolution or self-variation of virus. Since its pathogen has an entirely new biological structure, the disease is generally difficult to prevent and treat at its outbreak, and thus causes a very serious hazard. Influenza virus, due to its high variability and the susceptibility of human body thereto, becomes an important source for suddenly occurring new-type viral infectious disease. At regular intervals, new-type influenza will become widely pandemic in humankind. In recent 100 years, there have been at least four times of outbreak of influenza, among which the influenza pandemic in 1918 killed almost twenty millions of people around the world. At present, H5N1 type high pathogenic avian influenza is pervading in poultry, and this influenza, along with the discontinuous variation in itself, will necessarily become a new type of influenza that can infect humankind. As the threat of an outbreak of influenza is drawing near, it is a very important means to develop in time a high-efficiency drug for dealing with the prevalence of suddenly occurring new-type viral infectious disease led by new-type influenza.

Neuraminidase (NA) is a key protein that promotes the separation and diffusion of influenza virus particles as newly formed from infected cells. Among the three types of proteins (hemagglutinin, HA, neuraminidase, NA and nonstructural protein NS1) that are the easiest variable on the surface of influenza virus, NA is relatively stable, and in particular, the amino acid sequences thereof that constitute active sites are highly conservative in all influenza A and B viruses. Therefore, the development of an NA inhibitor is the optimal choice for dealing with unknown influenza virus. As far as the drugs for preventing and treating new type of influenza are concerned, NA inhibitors represented by oseltamivir and zanamivir are regarded as potential effective drugs. However, the two drugs both have certain limitations. Both of them are oral preparations, are unfavorable for treating high risk patients, and are also inconvenient to take by susceptible population such as elderly person and children, so their effects of prevention and treatment are greatly limited. As for other serious viral infectious diseases, there aren't effective drugs to prevent and treat them as well, and the expense for treating them is high. Moreover, the large and wide use of a single type of drug easily leads to the occurrence of drug-resistant virus stains, so that the drug prevention and treatment system will lose its protection ability. Therefore, it is necessary to continuously search for a new therapeutic route to thereby develop a drug having good therapeutic effect and low toxic-side effect.

(1S,2S,3S,4R)-3-[(1S)-1-acetylamino-2-ethyl-butyl]-4-guanidino-2-hydroxy-cyclopentyl-1-carboxylic acid [RWJ270201, BCX1812, JNJ2, peramivir] is a type of cyclopentane compound that is completely different in structure from oseltamivir and zanamivir, and can selectively inhibit NA of influenza A and B viruses. In vitro activity study showed that RWJ270201 could selectively inhibit in vitro the activity of NA of 7 influenza A virus stains (IC50=0.1-1.4 nM), and the activity of NA of 4 influenza B virus strains (IC50=0.6-11 nM) (Bania S., Parker C. D., Ananth S. L., et al, Comparison of the Anti-influenza Virus Activity of RWJ270201 against Clinical Isolates of Influenza Virus and Neuraminidase Inhibitor-Resistant Variants, Antimicrob Agents Chemother, 2001, 45(12), 3403-3408). The activity of RWJ270201 was equivalent to or higher than that of oseltamivir and zanamivir. In vivo activity study showed that RWJ270201 could markedly reduce the death rate of mice that were infected with influenza virus strain A/HongKong/156/97 (H5N1), resulting in a survival rate of up to 70% in the group of 0.1 mg/kg/day, and a survival rate of up to 100% in the group of 10 mg/kg/day, and could markedly reduce virus titer in lung tissue, and prevent the diffusion of virus to brain tissue (Govorkova E. A., Leneva I. A., Goloubeva O. G., et al., Comparison of Efficiencies of RWJ270201, Zanamivir, and Oseltamivir against H5N1, H9N2, and Other Avian Influenza Viruses, Antimicrob Agents Chemother, 2001, 45(10), 2723-2732). RWJ270201 could also inhibit lung consolidation and virus titer in lung tissue at the $6^{th}$ day, and acted for a longer period of time than oseltamivir. This compound could still prevent the reduction in arterial oxygen saturation at a dose as low as 1 mg/kg/day. RWJ270201 (1 mg/kg/day) could also reduce the death rate, inhibit lung consolidation and prevent the reduction in arterial oxygen saturation of laboratory animals infected with lethal influenza virus strain B/Hong Kong/5/72, and was more effective than oseltamivir. In addition, RWJ270201 at a dose of 10 mg/kg/day could also effectively antagonize the infection with lethal influenza virus strain A/Bayern/07/95 (H1N1), and reduce the death rate of laboratory animals infected with influenza virus strain A/NWS/33 (H1N1) (Bantia S., Amold C. S., Parker C. D., Anti-influenza Virus Activity of Peramivir in Mice with Single Intramuscular Injection, Antiviral Research, 2006, 69(1), 39-45). RWJ270201 had a low toxicity, and was non-toxic to cells at a dose as high as 328 µg/ml; no toxic side effect was found when RWJ270201 was administered to rats at a dose of 1000 mg/kg/day for 5 days. No acute toxic reaction was observed when the dose administered to mice and rats was up to 3000 mg/kg/day (Sidwell R. W., Smee D. F., Huffman J. H., et al., In the fluenza of Virus Strain, Challenge Dose, and Time of Therapy Initiation on the in vivo Influenza Inhibitory Effect of RWJ270201, Antiviral Res., 2001, 51(3), 179-187). RWJ270201 is a new kind of high-efficiency and low-toxicity NA inhibitor.

However, as shown by study, RWJ270201 is easily hygroscopic, and it is difficult to completely remove water therein after absorbing moisture, thus the anhydrous form of RWJ270201 is difficult to obtain in industry, and the quality thereof is difficult to effectively control. RWJ270201 is unstable in aqueous solution, is easy to self-degrade under the influence of environmental factors, and is difficult to directly prepare into an injection for treating severe patients. The object of the invention is just for searching for (1S,2S,3S,4R)-3-[(1S)-1-acetylamino-2-ethyl-butyl]-4-guanidino-2-hydroxy-cyclopentyl-1-carboxylic acid derivative which is not easily hygroscopic and is controllable in quality and a method for preparing the same, and simultaneously developing a corresponding injection for treating severe patients.

SUMMARY OF THE INVENTION

The present inventors discovered by study that (1S,2S,3S,4R)-3-[(1S)-1-acetylamino-2-ethyl-butyl]-4-guanidino-2-hydroxy-cyclopentyl-1-carboxylic acid hydrate (I) exhibits a good stability, and is not easily hygroscopic, easily controllable in quality, and suitable for large-scale industrial production, as compared to RWJ270201 and other derivatives.

The results of pharmacodynamic study demonstrated that (1S,2S,3S,4R)-3-[(1S)-1-acetylamino-2-ethyl-butyl]-4-guanidino-2-hydroxy-cyclopentyl-1-carboxylic acid hydrate (I) exhibited the same activity to many types of influenza virus strains in vivo and in vitro as RWJ270201. The results of drug metabolism demonstrated that (1S,2S,3S,4R)-3-[(1S)-1-acetylamino-2-ethyl-butyl]-4-guanidino-2-hydroxy-cyclopentyl-1-carboxylic acid hydrate (I) exhibited the same metabolic pathway and pharmacokinetic property as RWJ270201. The results of toxicological study demonstrated that (1S,2S,3S,4R)-3-[(1S)-1-acetylamino-2-ethyl-butyl]-4-guanidino-2-hydroxy-cyclopentyl-1-carboxylic acid hydrate (I) exhibited the same effect in various toxicity indexes as RWJ270201. Thus, (1S,2S,3S,4R)-3-[(1S)-1-acetylamino-2-ethyl-butyl]-4-guanidino-2-hydroxy-cyclopentyl-1-carboxylic acid hydrate (I) is equipotent to RWJ270201.

The present inventors further discovered by study that the stability of (1S,2S,3S,4R)-3-[(1S)-1-acetylamino-2-ethyl-butyl]-4-guanidino-2-hydroxy-cyclopentyl-1-carboxylic acid hydrate (I) in aqueous solution can be controlled by adjusting pH value of the solution, and a quite good stability can be obtained at a suitable pH value, whereby an injection suitable for treating severe patients is developed.

Therefore, on the one hand, the present invention provides a compound of the general formula (I), and a method for preparing it.

On the other hand, the present invention provides a pharmaceutical composition comprising the compound of the invention and a method for preparing it. The pharmaceutical composition of the invention comprises at least one compound of the general formula (I), and at least one pharmaceutically acceptable carrier, diluent or excipient.

Still on the other hand, the present invention provides a method for treating or preventing diseases, risk factors or symptoms caused by influenza virus, which comprises administering a therapeutically or preventively effective amount of the compound of the invention to a subject.

DETAILED DESCRIPTION OF THE INVENTION

The present invention provides (1S,2S,3S,4R)-3-[(1S)-1-acetylamino-2-ethyl-butyl]-4-guanidino-2-hydroxy-cyclopentyl-1-carboxylic acid hydrate expressed by the general formula (I)

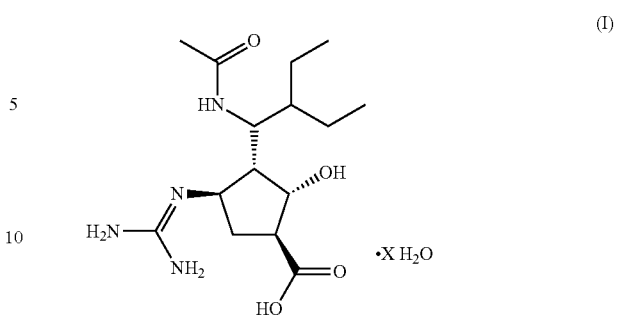

wherein X is 2.0 or 3.0.

The compound of the invention can inhibit the activity of NA of influenza virus.

According to one preferred embodiment, the preferred compound of the invention is (1S,2S,3 S,4R)-3-[(1S)-1-acetylamino-2-ethyl-butyl]-4-guanidino-2-hydroxy-cyclopentyl-1-carboxylic acid trihydrate.

According to the invention, the term "influenza virus" includes, but is not limited to, human influenza viruses and influenza viruses derived from various kinds of animals, e.g., avian influenza virus.

A person skilled in the art shall perceive that the compound of the invention can also be used in the form of its pharmaceutically acceptable salt. The pharmaceutically acceptable salt of the compound of the general formula (I) includes conventional salts formed with pharmaceutically acceptable inorganic acids or organic acids or inorganic bases or organic bases and acid addition salts of quaternary ammonium. Examples of suitable salts formed with acids include salts formed with hydrochloric acid, hydrobromic acid, sulfuric acid, phosphoric acid, nitric acid, perchloric acid, fumaric acid, acetic acid, propionic acid, succinic acid, hydroxyacetic acid, formic acid, lactic acid, maleic acid, tartaric acid, citric acid, pamoic acid, malonic acid, hydroxymaleic acid, phenylacetic acid, glutamic acid, benzoic acid, salicylic acid, toluenesulfonic acid, methanesulfonic acid, naphthalene-2-sulfonic acid, benzenesulfonic acid, hydroxyl naphthaleneformic acid, hydroiodic acid, malic acid, steroic acid, tannic acid and etc. As for other acids, such as oxalic acid, although being not pharmaceutically acceptable by themselves, they can be used for preparing salts as intermediates, to thereby obtain the compound of the invention and pharmaceutically acceptable salts thereof. Examples of suitable salts formed with bases include salts formed with sodium, lithium, potassium, magnesium, aluminum, calcium, zinc, N,N'-dibenzylethylenediamine, chloroprocaine, choline, diethanolamine, ethylenediamine, N-methylglucosamine and procaine. The compound of the invention as mentioned hereinbelow includes compound of the general formula (I) and pharmaceutically acceptable salts thereof.

The present invention further includes a prodrug of the compound of the invention, which, once administered, undergoes a chemical conversion through metabolic process, to convert into an active drug. Generally, this kind of drug is a functional derivative of the compound of the invention, and easily converts into the desired compound of the general formula (I) in vivo. For example, conventional methods for selecting and preparing suitable prodrug derivatives are described in "Design Of Prodrugs", H Bund Saard, Elsevier, 1985.

The present invention also includes active metabolites of the compound of the invention.

On the other hand, the present invention relates to a pharmaceutical composition comprising the compound of the invention and at least one pharmaceutically acceptable carrier, diluent or excipient, which can be used for in vivo treatment and has biocompatibility. The pharmaceutical composition can be prepared into various forms according to different administration routes.

The pharmaceutical composition of the invention comprises an effective amount of the compound of the general formula (I) or a pharmaceutically acceptable salt thereof, and one or more suitable pharmaceutically acceptable carrier, diluent or excipient. The pharmaceutically acceptable carrier, diluent or excipient includes, but is not limited to, ion exchanger, aluminum oxide, aluminum stearate, lecithin, serum protein such as human albumin, buffer substance such as phosphate, glycerin, sorbic acid, potassium sorbate, a mixture of partial glycerides of saturated vegetable fatty acid, water, salt or electrolyte such as protamine sulfate, disodium hydrogen phosphate, potassium hydrogen phosphate, sodium chloride, zinc salt, colloidal silica, magnesium trisilicate, polyvinylpyrrolidone, cellulosic material, polyethylene glycol, sodium carboxymethylcellulose, polyacrylate, beeswax, lanolin.

The pharmaceutical composition of the invention may be administered in any of the following routes: orally, spray inhalation, rectally, nasally, buccally, topically, parenterally such as subcutaneous, intravenous, intramuscular, intraperitoneal, intrathecal, intraventricular, intrasternal or encephalic injection or infusion, or administered with the aid of an explanted reservoir, wherein the administration routes by parenteral route such as intravenous injection are preferred.

For oral administration, the compound of the invention may be made into any orally acceptable preparation forms, including, but not limited to, tablets, capsules, aqueous solutions or aqueous suspensions. Wherein, carrier used in tablets generally includes lactose and corn starch, to which lubricant such as magnesium stearate may also be added. Diluent used in capsule preparation generally includes lactose and dried corn starch. Aqueous suspension preparation is generally used by mixing active ingredient with suitable emulsifying agent and suspending agent. If desired, a sweetening agent, a flavoring agent or a colorant may be added.

For topical application, in particular for treating the affected face or organ that is easy to reach by topically external application, e.g., eyes and skin, the compound of the invention may be made into different preparation forms for topical application according to the different affected face or organ.

For topical application on eyes, the compound of the invention may be made into the preparation form of a micronized suspension or solution, wherein the carrier used is an isotonic sterile brine having a certain pH value, and wherein an antiseptic such as chlorinated benzyl alkoxide may be added or not. For eye use, the compound may also be made into the preparation form of paste such as vaseline paste.

For topical application on skin, the compound of the invention may be made into a suitable form of ointment, lotion or cream, wherein the active ingredient is suspended or dissolved in one or more carrier(s). The carrier used for an ointment includes, but not limited to, mineral oil, liquid vaseline, white vaseline, propylene glycol, polyethylene oxide, polypropylene oxide, emulsified wax and water; the carrier used for a lotion and a cream includes, but not limited to, mineral oil, sorbitan monostearic ester, Tween 60, cetyl esters wax, hexadecylene aromatic alcohol, 2-octyl dodecanol, benzanol and water.

The compound of the invention may also be administered in the form of sterile injection preparation, including, but not limited to, sterile injection aqueous or oil suspension or sterile injection solution or sterile powder injection such as lyophilized powder injection. Wherein, the useable carrier and solvent include water, Ringer's solution and isotonic sodium chloride solution. In addition, sterilized non-volatile oil such as monoglyceride or diglyceride may also be used as solvent or suspending medium. In addition, the preparation may further include a pH adjusting agent, 0.9% aqueous solution of sodium chloride, a buffer, an antioxidant, a metal ion complexing agent, or any combinations thereof.

Further, the administration dosage and manner of the compound of the invention depend on various factors, such as age, body weight, gender, natural health status and nutrient status of the patient, activity of the compound, administration time, metabolic rate, degree of severity of the disease, and subjective judgment made by a doctor for diagnosis/treatment. The administration dosage is preferably within the range of 0.01-100 mg/kg body weight/day, and most preferably within the range of 1-40 mg/kg body weight/day.

The present invention further provides a method for preparing the compound of the general formula (I).

The patent applications CN1282316A (2001), CN1367776A (2002) disclose a method for preparing the (1S,2S,3S,4R)-3-[(1S)-1-acetylamino-2-ethyl-butyl]-4-guanidino-2-hydroxy-cyclopentyl-1-carboxylic acid crude product, but the raw materials and the catalysts used therein are expensive, and hypertoxic benzyl isocyanate is used therein, thus the method is not suitable for industrial production.

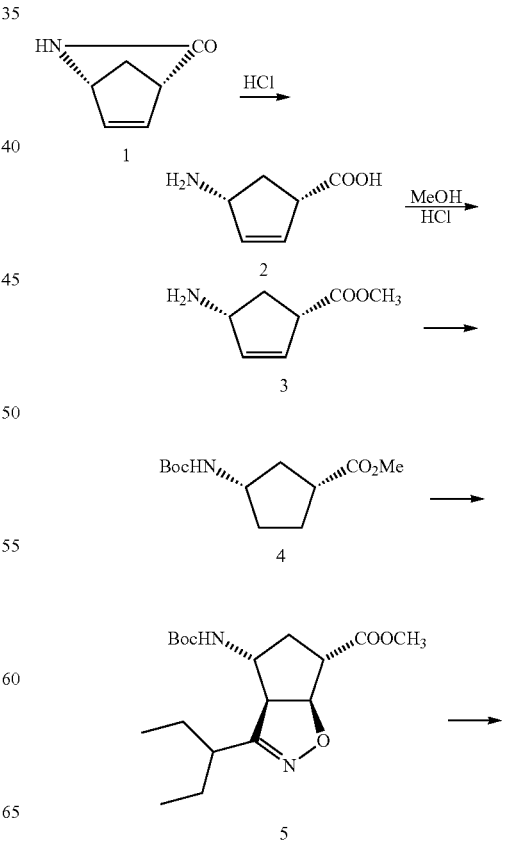

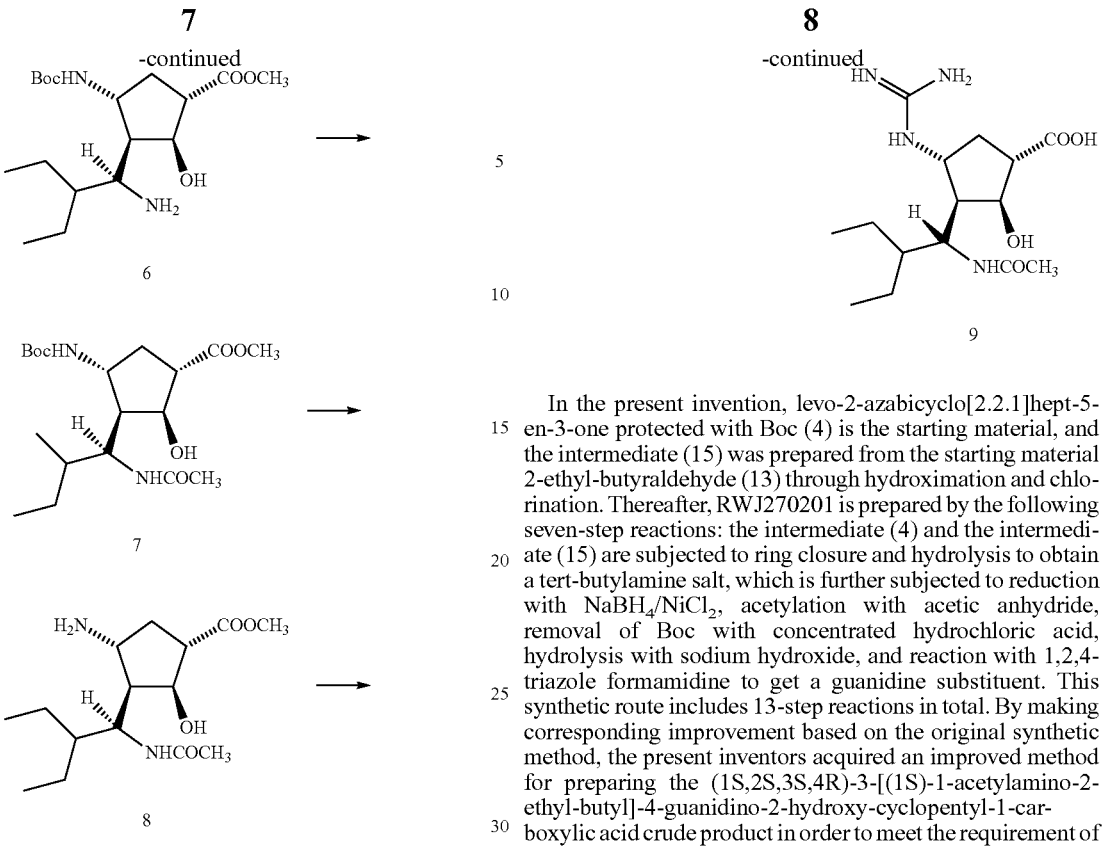

In the present invention, levo-2-azabicyclo[2.2.1]hept-5-en-3-one protected with Boc (4) is the starting material, and the intermediate (15) was prepared from the starting material 2-ethyl-butyraldehyde (13) through hydroximation and chlorination. Thereafter, RWJ270201 is prepared by the following seven-step reactions: the intermediate (4) and the intermediate (15) are subjected to ring closure and hydrolysis to obtain a tert-butylamine salt, which is further subjected to reduction with $NaBH_4/NiCl_2$, acetylation with acetic anhydride, removal of Boc with concentrated hydrochloric acid, hydrolysis with sodium hydroxide, and reaction with 1,2,4-triazole formamidine to get a guanidine substituent. This synthetic route includes 13-step reactions in total. By making corresponding improvement based on the original synthetic method, the present inventors acquired an improved method for preparing the (1S,2S,3S,4R)-3-[(1S)-1-acetylamino-2-ethyl-butyl]-4-guanidino-2-hydroxy-cyclopentyl-1-carboxylic acid crude product in order to meet the requirement of industrialized production.

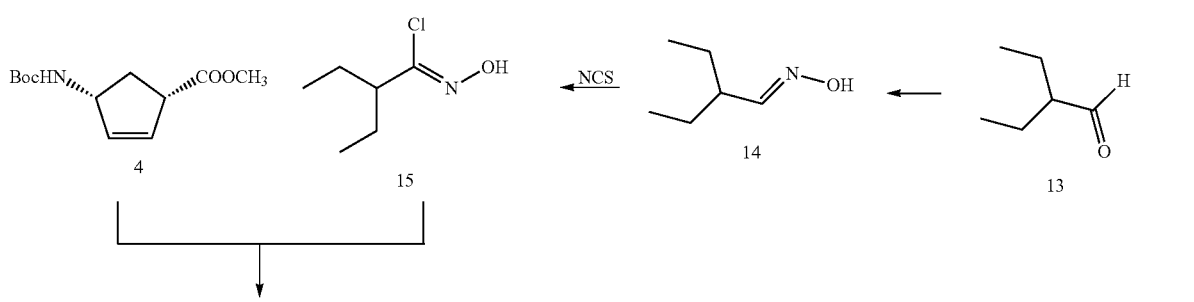

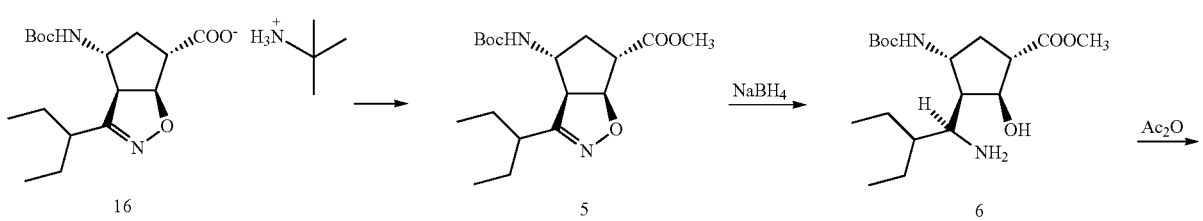

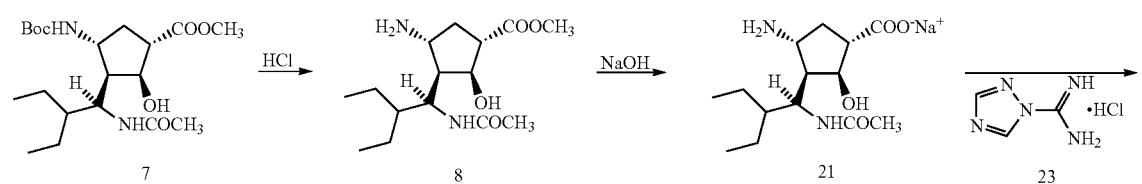

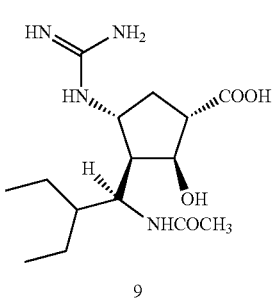

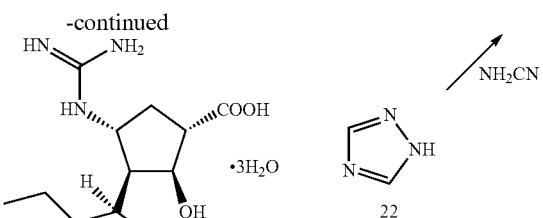

In the method of the present invention, the (1S,2S,3S,4R)-3-[(1S)-1-acetylamino-2-ethyl-butyl]-4-guanidino-2-hydroxy-cyclopentyl-1-carboxylic acid crude product is dissolved in a solution consisting of water and a water-miscible organic solvent in different ratios under a suitable temperature typically in the range of 20-100° C., preferably 80-100° C., wherein the organic solvent includes, but is not limited to, methanol, ethanol, n-butanol, acetone, butanone, tert-butanone and etc., and the ratio of water:organic solvent is 100:1-500, or under the condition of pure water, preferably in the range of 20:1 to 1:2; and then the resulting solution is subjected to crystallization at a suitable cooling rate, e.g., from 0.1° C./min to 5° C./minute, to obtain (1S,2S,3S,4R)-3-[(1S)-1-acetylamino-2-ethyl-butyl]-4-guanidino-2-hydroxy-cyclopentyl-1-carboxylic acid hydrates (I) containing different crystal water. The compound of the general formula (I) of the invention may also be obtained by adding crystal seed of the compound of the general formula (I) under the aforementioned conditions.

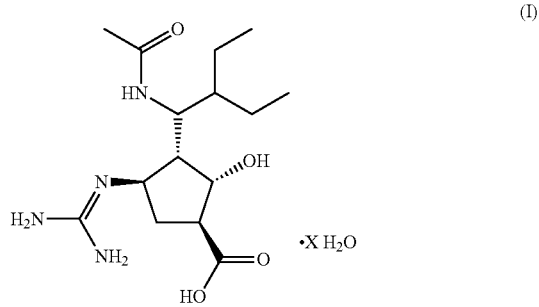

wherein X is 2.0 or 3.0.

The preferred compound of the invention is (1S,2S,3S,4R)-3-[(1S)-1-acetylamino-2-ethyl-butyl]-4-guanidino-2-hydroxy-cyclopentyl-1-carboxylic acid trihydrate.

According to the invention, the solubility of the compound of the invention can be tested by using a standard solubility test method. For example, in room-temperature aqueous solution and in neutral buffer solution, (1S,2S,3S,4R)-3-[(1S)-1-acetylamino-2-ethyl-butyl]-4-guanidino-2-hydroxy-cyclopentyl-1-carboxylic acid trihydrate, as one of the compounds of the general formula (I), has a solubility 0.17 g/ml, and the (1S,2S,3S,4R)-3-[(1S)-1-acetylamino-2-ethyl-butyl]-4-guanidino-2-hydroxy-cyclopentyl-1-carboxylic acid crude product has a solubility 0.08 g/ml. Therefore, the compound of the general formula (I) exhibits an obviously increased solubility in aqueous solution and in neutral physiological buffer solution compared to the corresponding non-hydrate.

The hygroscopicity of the compound of the invention can be tested by a standard hygroscopicity test method. For example, the compound is stored in a sealed vessel at room temperature at a relative humidity of 92.5%, 80% or 75%, and the change in moisture content of the compound is tested by sampling at regular intervals. In a ten-day observation test, it is found that (1S,2S,3S,4R)-3-[(1S)-1-acetylamino-2-ethyl-butyl]-4-guanidino-2-hydroxy-cyclopentyl-1-carboxylic acid trihydrate, as one of the compounds of the general formula (I), has a weight gain of about 2.24%, while the (1S,2S,3S,4R)-3-[(1S)-1-acetylamino-2-ethyl-butyl]-4-guanidino-2-hydroxy-cyclopentyl-1-carboxylic acid crude product has a weight gain of about 13.53%. Therefore, the compound of the general formula (I) exhibits an obviously reduced hygroscopicity under high wet conditions compared to the corresponding non-hydrate.

The stability of the compound of the invention can be tested by a standard stability test method, such as the methods specified in Guidelines for Stability Testing of Drug Substances involved in Appendix XIX C of Chinese Pharmacopoeia (2005 edition). For example, the stability of the compound of the general formula (I) can be tested by an accelerated stability test method, e.g., the stability of the compound of the general formula (I), at 0, 1, 2, 3, 6 months, is tested respectively under the conditions: 40° C., 75% relative humidity; 40° C., 92.5% relative humidity; and 80° C. The change in principal agent and relevant substances can be analyzed by thin layer chromatography, high performance liquid chromatography, and etc. In the stability test of 1, 2, 3, 6 months, (1S,2S,3S,4R)-3-[(1S)-1-acetylamino-2-ethyl-butyl]-4-guanidino-2-hydroxy-cyclopentyl-1-carboxylic acid trihydrate, as one of the compounds of the general formula (I), has a stable content of the principal agent, and no notable increase in the content of the relevant substances, and exhibits a good stability.

The (1S,2S,3S,4R)-3-[(1S)-1-acetylamino-2-ethyl-butyl]-4-guanidino-2-hydroxy-cyclopentyl-1-carboxylic acid hydrates as obtained in the present invention exhibit a good stability, and are not easily hygroscopic, and are easily controllable in quality and suitable for large-scale industrialized production.

The present invention further relates to a pharmaceutical composition for preventing and treating influenza comprising the compound of the general formula (I) and a pharmaceutically acceptable carrier.

The compound of the general formula (I) herein may be used alone or in the form of a pharmaceutical composition. The pharmaceutical composition of the invention can be administered by oral, parenteral or topical administration routes. Examples of the administration dosage form include, but are not limited to, tablets, capsules, solutions, injections, suppositories, patches, ointments, and etc. The preferred dosage form is the pharmaceutical composition for parenteral administration and powder injection preparation.

In order to enable the compound of the general formula (I) to be suitable for emergency aid and treatment of severe patients with influenza, the present inventors by study developed pharmaceutical composition for parenteral administration and powder injection preparation having multiple advantages. Moreover, their preparation method is simple, easy to operate, and low in cost.

In the present invention, the amount of the compound of the general formula (I) or the amount of the compound of the general formula (I) in the pharmaceutical composition is calculated by (1S,2S,3S,4R)-3-[(1S)-1-acetylamino-2-ethyl-butyl]-4-guanidino-2-hydroxy-cyclopentyl-1-carboxylic acid.

In concrete, the pharmaceutical composition for parenteral administration is characterized by comprising a pharmaceutically acceptable solvent and from about 50% to about 4000% w/v of the compound of the general formula (I), wherein the amount of the compound of the general formula (I) in the pharmaceutical composition is calculated by the amount of (1S,2S,3S,4R)-3-[(1S)-1-acetylamino-2-ethyl-butyl]-4-guanidino-2-hydroxy-cyclopentyl-1-carboxylic acid, and w/v refers to the ratio of the weight of the compound of the general formula (I) to the volume of the solvent in unit dosage form. The (1S,2S,3 S,4R)-3-[(1S)-1-acetylamino-2-ethyl-butyl]-4-guanidino-2-hydroxy-cyclopentyl-1-carboxylic acid hydrate of the general formula (I) is present in an amount of preferably from 300% to 2000% w/v on the basis of the composition. The composition may further optionally comprise at least one ingredient selected from a pH adjusting agent, a buffer, an antioxidant, a metal ion complexing agent, or any combinations thereof. The pH adjusting agent therein is selected from inorganic acids, and is present in an amount sufficient to adjust the pH value of the composition to about 3-7. The pH adjusting agent is preferably diluted hydrochloric acid, and is preferably present in an amount sufficient to adjust the pH value of the composition to about 4-6. The pharmaceutically acceptable solvent is selected from the group consisting of water, 0.9% aqueous solution of sodium chloride, PEG400, propylene glycol, ethanol, glycerin and any combinations thereof, preferably water. In the composition which comprises water as solvent, the (1S,2S,3S,4R)-3-[(1S)-1-acetylamino-2-ethyl-butyl]-4-guanidino-2-hydroxy-cyclopentyl-1-carboxylic acid hydrate of the general formula (I) is present in an amount of preferably from 300 mg/100 ml to 100 mg/5 ml on the basis of the composition.

The powder injection preparation is characterized by comprising the (1S,2S,3 S,4R)-3-[(1S)-1-acetylamino-2-ethyl-butyl]-4-guanidino-2-hydroxy-cyclopentyl-1-carboxylic acid hydrate of the general formula (I), or additionally comprising at least one of the following pharmaceutically acceptable carriers: a pH adjusting agent, a buffer, an antioxidant, a metal ion complexing agent, or any combinations thereof. The carrier includes, but is not limited to, dextro-glucoside, mannitol, sodium chloride, sorbitol, citric acid and etc. The commonly used pH adjusting agent includes, but is not limited to, hydrochloric acid, phosphoric acid, fumaric acid, acetic acid, propionic acid, succinic acid, maleic acid, tartaric acid, citric acid, hydroxymaleic acid, glutamic acid, salicylic acid and etc., preferably hydrochloric acid. The weight ratio of (1S,2S,3S,4R)-3-[(1S)-1-acetylamino-2-ethyl-butyl]-4-guanidino-2-hydroxy-cyclopentyl-1-carboxylic acid trihydrate to the pharmaceutically acceptable carrier in unit dose is 1:0-1:100, and the pH adjusting agent is used in an amount sufficient to assure that, when the preparation is used in unit dose, the solution has a pH ranging from 2.5 to 6.5, preferably ranging from 3.5 to 5.5.

The above preparation is preferably used for clinical application in the form of intravenous or intramuscular injection, or intravenous drip infusion.

On the other hand, the present invention further provides a method for preparing the pharmaceutical composition for parenteral administration comprising the (1S,2S,3 S,4R)-3-[(1S)-1-acetylamino-2-ethyl-butyl]-4-guanidino-2-hydroxy-cyclopentyl-1-carboxylic acid hydrate, which comprises dissolving the compound of the general formula (I), adsorbing with activated carbon and filtering, adjusting the acidity, fine filtrating, filling and high-pressure high-temperature sterilizing, and etc., or making the compound of the general formula (I), according to a method known in the art, into a powder injection such as lyophilized powder injection.

According to one embodiment in the present invention, the pharmaceutical composition for parenteral administration, per ml, comprises 0.5 mg to 4 g of (1S,2S,3 S,4R)-3-[(1S)-1-acetylamino-2-ethyl-butyl]-4-guanidino-2-hydroxy-cyclopentyl-1-carboxylic acid hydrate of the general formula (I), and at least one of the following pharmaceutically acceptable carriers: a pH adjusting agent, 0.9% aqueous solution of sodium chloride, a buffer, an antioxidant, a metal ion complexing agent, or any combinations thereof.

The pharmaceutical composition for parenteral administration comprising the (1S,2S,3S,4R)-3-[(1S)-1-acetylamino-2-ethyl-butyl]-4-guanidino-2-hydroxy-cyclopentyl-1-carboxylic acid hydrate of the general formula (I) herein may be prepared by the following method comprising the steps of:

(1) dissolving the (1S,2S,3S,4R)-3-[(1S)-1-acetylamino-2-ethyl-butyl]-4-guanidino-2-hydroxy-cyclopentyl-1-carboxylic acid hydrate of the general formula (I) in a pharmaceutically acceptable solvent selected from water, 0.9% aqueous solution of sodium chloride, PEG400, propylene glycol, ethanol, glycerin or any combinations thereof, by stirring at room temperature, ultrasonic dissolution, or heating to 40-100° C.;

(2) adding 0.01% to 5% of activated carbon at 40-100° C. to carry out adsorption treatment for 10 to 30 minutes, and filtering;

(3) adding a pH adjusting agent in an amount sufficient to adjust the pH value of the solution to about 4-6;

(4) filtering with a fine filtration membrane and filling by a volume of 1 to 150 ml per unit; and (5) sealing and sterilizing at 105 to 125° C. for 10 to 50 minutes.

According to another embodiment in the present invention, the pharmaceutical composition for parenteral administration comprising the (1S,2S,3S,4R)-3-[(1S)-1-acetylamino-2-ethyl-butyl]-4-guanidino-2-hydroxy-cyclopentyl-1-carboxylic acid hydrate of the general formula (I) comprises:

(1) from 300% to 2000% w/v of the (1S,2S,3S,4R)-3-[(1S)-1-acetylamino-2-ethyl-butyl]-4-guanidino-2-hydroxy-cyclopentyl-1-carboxylic acid hydrate of the general formula (I);

(2) a pharmaceutically acceptable solvent selected from water, PEG400, propylene glycol, ethanol, glycerin or any combinations thereof, preferably water; and (3) a pH adjusting agent, preferably diluted hydrochloric acid, preferably present in an amount sufficient to adjust the pH value of the composition to about 4-6.

According to still another embodiment in the present invention, the pharmaceutical composition for parenteral administration comprising the (1S,2S,3S,4R)-3-[(1S)-1-acetylamino-2-ethyl-butyl]-4-guanidino-2-hydroxy-cyclopentyl-1-carboxylic acid hydrate of the general formula (I) comprises:

(1) from 300% to 2000% w/v of the (1S,2S,3S,4R)-3-[(1S)-1-acetylamino-2-ethyl-butyl]-4-guanidino-2-hydroxy-cyclopentyl-1-carboxylic acid hydrate of the general formula (I);

(2) a pharmaceutically acceptable solvent selected from water, 0.9% aqueous solution of sodium chloride, PEG400, propylene glycol, ethanol, glycerin or any combinations thereof, preferably 0.9% aqueous solution of sodium chloride; and (3) a pH adjusting agent, preferably diluted hydrochloric acid, preferably present in an amount sufficient to adjust the pH value of the composition to about 4-6.

The most preferred formulation of the pharmaceutical composition for parenteral administration is shown in the examples.

Still on the other hand, the present invention provides a method for preparing a powder injection preparation of (1S,2S,3S,4R)-3-[(1S)-1-acetylamino-2-ethyl-butyl]-4-guanidino-2-hydroxy-cyclopentyl-1-carboxylic acid trihydrate, i.e., a powder injection preparation comprising the (1S,2S,3S,4R)-3-[(1S)-1-acetylamino-2-ethyl-butyl]-4-guanidino-2-hydroxy-cyclopentyl-1-carboxylic acid trihydrate as active ingredient. This powder injection preparation is prepared by dissolving (1S,2S,3S,4R)-3-[(1S)-1-acetylamino-2-ethyl-butyl]-4-guanidino-2-hydroxy-cyclopentyl-1-carboxylic acid trihydrate in at least one solvent selected from water for injection, ethanol and ethyl ether, and then subjecting the resulting solution to dehydration or desolvation.

According to one embodiment in the present invention, the powder injection preparation, per gram, comprises from 0.1 mg to 1 g of (1S,2S,3S,4R)-3-[(1S)-1-acetylamino-2-ethyl-butyl]-4-guanidino-2-hydroxy-cyclopentyl-1-carboxylic acid trihydrate, or additionally comprises at least one of the following filling agents: a pH adjusting agent, a buffer, an antioxidant, a metal ion complexing agent, or any combinations thereof.

The powder injection preparation of (1S,2S,3S,4R)-3-[(1S)-1-acetylamino-2-ethyl-butyl]-4-guanidino-2-hydroxy-cyclopentyl-1-carboxylic acid trihydrate herein may be prepared by the following method comprising the steps of:

dissolving (1S,2S,3S,4R)-3-[(1S)-1-acetylamino-2-ethyl-butyl]-4-guanidino-2-hydroxy-cyclopentyl-1-carboxylic acid trihydrate with at least one pharmaceutically acceptable solvent including, but not limited to, water for injection, ethanol and ethyl ether to obtain a solution having a concentration range of 1-6 g/100 ml, preferably 2.3-3.5 g/100 ml; adjusting the solution with an organic acid or inorganic acid to a pH range of 2.5-6.5, preferably a pH range of 3.5-5.5, wherein the inorganic acid and organic acid as commonly used include hydrochloric acid, phosphoric acid, fumaric acid, acetic acid, propionic acid, succinic acid, maleic acid, tartaric acid, citric acid, hydroxymaleic acid, glutamic acid, salicylic acid and etc., preferably hydrochloric acid; decolorating the solution with a pharmaceutically acceptable activated carbon; filtering with a 0.22 μm microporous filtration membrane; and then drying to obtain a sterile powder injection preparation of (1S,2S,3S,4R)-3-[(1S)-1-acetylamino-2-ethyl-butyl]-4-guanidino-2-hydroxy-cyclopentyl-1-carboxylic acid trihydrate, wherein the drying is carried out by a vacuum drying method, a lyophilization method, a spray drying method or a freezing and filling method.

The pharmaceutical composition for parenteral administration is featured with high temperature resistance, storability, high stability, and ability of effectively overcoming self-degradation in aqueous solution. The powder injection preparation is featured with advanced preparation method, good stability, long period of validity, convenience to transport, and easy to store and preserve. These products have the advantageous including safe and convenient to use, reliable quality, and easy to use for emergency aid and treatment of severe patients.

The inhibitory activity of the compound of the general formula (I) against neuraminidase can be assayed according to the method given by Barnett J M and et al (Barnett J M, et al. Antimicrob Agents Chem., 2000; 41, 78-87.). The method is described as follows:

Using 4-MUNANA as a substrate, the activity of influenza virus neuraminidase and the inhibitory activity of the candidate compound against neuraminidase are assayed by fluorimetry. A stock solution of first generation viruses is cultivated in MDCK cells, and diluted with a neuraminidase assay buffer (NA assay buffer: 32.5 MES, 4 mM $CaCl_2$, Ph 6.5) in a ratio of 1:2. 50 μl of the resulting virus diluted solution is mixed with equal volume of 4-MUNANA (200 mM in NA assay buffer) in a black 96-well plate (Costar), and incubated at 37° C. for 1 hour, and then 2 times by volume of a stop buffer (25% ethanol, 0.1M glycine, pH10.7) is added to stop the reaction. The fluorescence intensities at $\lambda$ Excitation: 360 nM and $\lambda$ Emission: 460 nM are assayed (PolarSTAR Optima, BMG Labtech, Germany). A scatter diagram of net value of fluorescence unit vs. virus concentration is plotted, and different virus concentrations, generally not less than two, with activity lying in the middle of the linear part of the scatter diagram are selected and used for the assay of the inhibitory activity of the compound. Solutions of candidate compounds having different concentrations are formulated using sterile deionized water. 25 μA of the respective solutions are mixed with equal amount of viruses (in a concentration two times of that selected in the activity assay) that have been diluted with 2×NA assay buffer, followed by acting at room temperature for 30 minutes, and then 50 μl of 4-MUNANA (200 mM in NA assay buffer) is added, followed by incubating at 37° C. for 1 hour, and finally the fluorescence intensity is assayed as above described. Each of the concentrations of the candidate compound is provided in two parallel holes, the blank control is provided in 4 parallel holes, which only includes 4-MUNANA and the stop buffer, and the virus control is provided in 4 parallel holes, which contains the candidate compound in a concentration of zero. The inhibitory rate IR (%) is calculated according to the following equation:

$$IR\ (\%)=[1-(FU-FUB)\div(FUC-FUB)]\times100$$

FU: average value of fluorescence unit in the candidate compound group;

FUB: average value of fluorescence unit in the blank control group;

FUC: average value of fluorescence unit in the virus control group.

A scatter diagram of IR (%) vs. concentration of compound is plotted, and $IC_{50}$ is calculated by logarithmic regression analysis. The regression curves obtained from the assay results of different virus concentrations shall preferably overlap, with similar $IC_{50}$ values.

The anti-influenza virus activity of the compound of the general formula (I) can be assayed according to the following method.

A virus drip is prepared typically by including 500 pfu (plaque forming unit) of mice-compliance influenza virus strain in 50 μl phosphate buffer (containing 0.42% bovine serum albumin), and then dropped into nasal cavity of mice to infect them (BALB/C, female, aged 5-6 weeks, weighted 20 g). The compound of the invention is suspended in physiological saline to obtain different doses, typically from 2.5 mg/kg to 40 mg/kg, and is administered to the mice at different time before and after the viral infection, typically administered by intraperitoneal injection for 5 times, i.e., 1 hour, and 2, 3, 4, 5 days after the viral infection. The assay is performed by using 8 or 12, typically 10 mice. The result is expressed by the ratio of the number of survival mice the 14th day after the viral infection to the number of the mice in assay. Meanwhile, anhydrous (1S,2S,3 S,4R)-3-[(1S)-1-acetylamino-2-ethyl-butyl]-4-guanidino-2-hydroxy-cyclopentyl-1-carboxylic acid is used as a control compound. The results show that the compound of the invention and the control compound exhibit the same or similar activity with respect to multiple types of influenza virus strains.

MODE OF CARRYING OUT THE PRESENT INVENTION

Examples

Example 1

Synthesis of 2-ethyl-N-hydroxybutyrimidoyl chloride (intermediate 15)

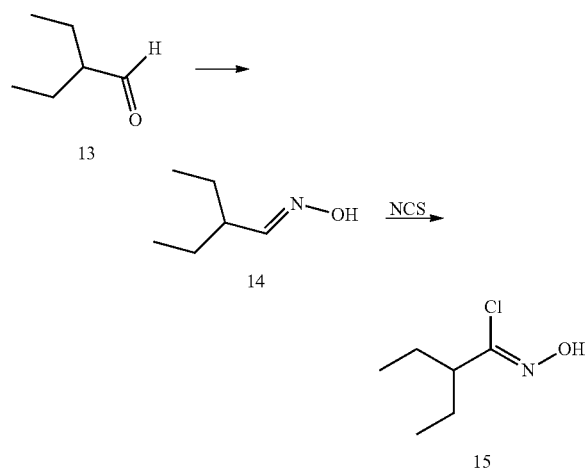

1150 g of hydroxylamine hydrochloride, 1000 g of water and 3500 g of toluene were mixed, to which 1580 g of 2-ethyl-butyraldehyde was added with stirring. At 8-12° C., a solution of sodium hydroxide (ca. 30%, 4630 g) was added within 1 hour. After completion of the addition, the reaction mixture was further stirred for 60 minutes. Then, the reaction mixture was stratified by standing, and the upper toluene layer containing compound 14 was taken out and directly used in the following step. 4212 g of N-Chlorosuccinimide (NCS) was suspended in 5000 ml of dimethylformamide, and cooled down to 8° C. The suspension of NCS in dimethylformamide was added dropwise to the above toluene solution containing compound 14 within 2.5 hours, whilst keeping the reaction temperature not exceeding 23° C. After completion of the addition, the reaction mixture was further stirred for 1 hour. Then, 10000 ml of water was added, followed by stirring for 30 minutes. The aqueous layer was discarded, and the organic layer was washed with 10000 ml×3 of water. The toluene layer containing compound 15 (chloro-oxime) was separated, and directly used in the following step.

Example 2

Synthesis of tert-butyl ammonium (3aR,4R,6S,6a5)-4-[[(1,1-dimethylethoxy)carbonyl]amino]-3-(1'-ethylpropyl)-3a,5,6,6a-tetrahydro-4H-cyclopenta[d]isooxazole-6-carboxylate (intermediate compound 16)

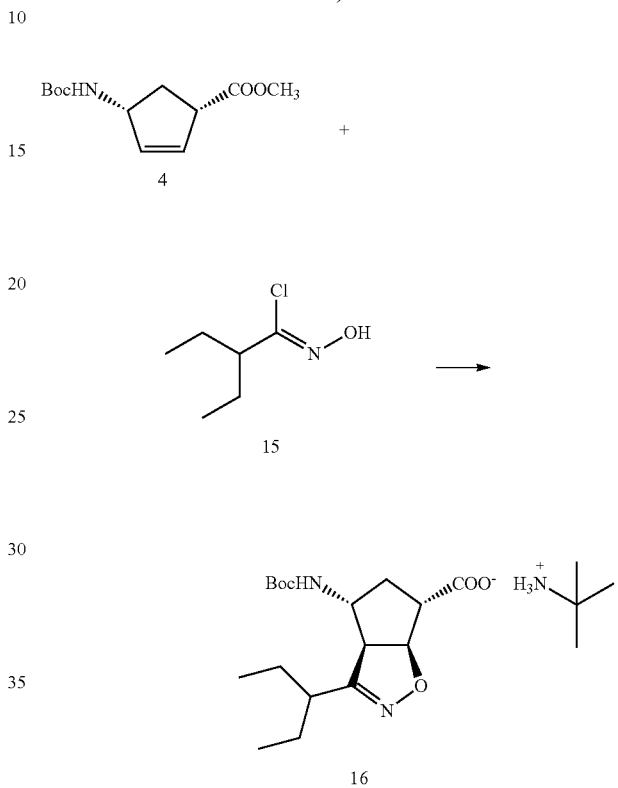

Methyl (1S,4R)-(−)-methyl-[[(1,1-dimethylethoxy)carbonyl]amino]cyclopent-2-ene-1-carboxylate (4) (2533.2 g), toluene (6000 ml) and triethylamine (4427 ml) were mixed and heated to 50° C. A solution of 2-ethyl-N-hydroxybutyrimidoyl chloride (compound 15, 4690 g) in toluene (6000 ml) was added dropwise to the resulting solution within 2.5 hours. After completion of the addition, the reaction mixture was further stirred at 62-66° C. for about 8 hours. 5000 ml of water was added into the reaction solution to dissolve solid. The toluene layer was separated, washed with 5000 ml of water, and then concentrated to remove about one half of toluene. A solution of sodium hydroxide (640 g, 16.0 mol) in water (4180 g) was added to the resulting concentrated solution, followed by stirring at room temperature for 7 hours. The toluene layer was discarded, and the aqueous layer was washed with 5000 ml×2 of toluene. 8000 ml of toluene was added to the aqueous phase. 3710 ml of water was added to 1747 ml of hydrochloric acid, and the diluted hydrochloric acid was added to the above toluene layer to neutralize it to a pH of about 4. Then, toluene (about 12000 ml) was added to dissolve solid, and toluene layer was separated. At 20-40° C., tert-butylamine (894.0 g) was added dropwise to the toluene layer, so that a white solid product was precipitated, followed by heating at 95-100° C. for 3 hours, and cooling down to 20-25° C. After suction filtration, the resulting solid product was washed with 8000 ml×2 of acetone, dried at 60° C. for 6 hours. Finally, 2694 g of a solid product was obtained, with a yield of 62.0%.

Example 3

Synthesis of methyl (3aR,4R,6S,6aS)-4-[[(1,1-dimethylethoxy)carbonyl]amino]-3-(1'-ethylpropyl)-3a,5,6,6a-tetrahydro-4H-cyclopenta[d]isooxazole-6-carboxylate (5)

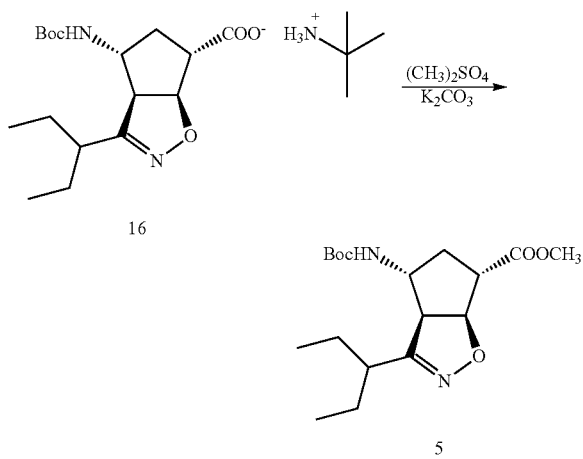

1,1-dimethylethyl ammonium (3aR,4R,6S,6aS)-4-[[(1,1-dimethylethoxy)carbonyl]amino]-3-(1'-ethylpropyl)-3a,5,6,6a-tetrahydro-4H-cyclopenta[d]isooxazole-6-carboxylate (16) (3210 g, 7.8 mol) was suspended in acetone (4000 g). Potassium carbonate (53.8 g), and an aqueous solution of 30% sodium hydroxide containing 312 g of sodium hydroxide were added to the resulting suspension. 3000 ml of solvent was removed by evaporation, 3000 ml of acetone was added, then, 3000 ml of solvent was removed by evaporation, 3000 ml of acetone was added, and thereafter 4000 ml acetone was removed by evaporation, obtaining a reaction solution substantially free of the odor of tert-butylamine. The reaction solution was cooled down to 30-35° C., to which 1060 ml of dimethyl sulfate was added dropwise at a speed to keep the temperature not exceeding 45° C. After completion of the addition, the resulting reaction mixture was stirred at 40-45° C. for 1.5 hours. The reaction mixture was cooled down to 15-20° C., to which was then added 1500 ml of 25% ammonia. After stirring for 30 minutes, 1500 ml of methanol was added, and then the reaction mixture was cooled down to 0-5° C. Thereafter, 2240 ml of 25% ammonia was added to the reaction mixture within 45 minutes. The resulting product was collected by filtration, washed with 3000 ml of water, and dried under vacuum at 45-50° C. Finally, 2686.2 g of a product was obtained, with a yield of 97.13%.

Example 4

Synthesis of methyl (1S,2S,3 S,4R,1'S)-3-[(1-amino-2'-ethyl)butyl]-4-[[(1,1-dimethylethoxy)carbonyl]amino]-2-hydroxycyclopentane-1-carboxylate (6)

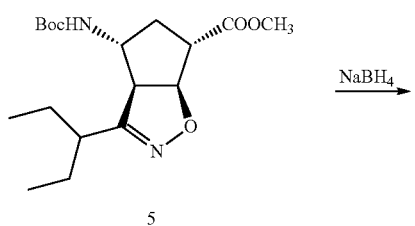

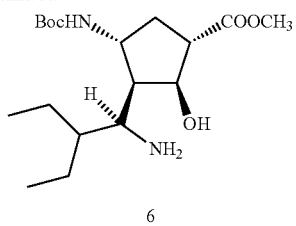

Intermediate 5 (1000 g) and nickel chloride hexahydrate (700 g) were dissolved in methanol (2500 ml), and cooled down to −10~5° C. Sodium hydroxide (5 g) and sodium borohydride (300 g) were dissolved in methanol (2300 ml), and added to the above reaction solution within about 4-6 hours, whilst keeping the temperature of the reaction solution in the range of −10~4° C. After completion of the addition, the reaction solution was stirred at 0~5° C. for 60 minutes. A solution formed by sodium nitrite (200 g), ammonium chloride (560 g) and 25% ammonia (650 g) with water (6000 ml) was added to the reaction solution. The reaction solution was then stirred at room temperature for 16 hours. Thereafter, the reaction solution was subjected to suction filtration, and the filter cake obtained was washed with a solution formulated by 25% ammonia (340 g) and water (2500 g) for 2 times. The filter cake was suspended in toluene (15000 ml) and 25% ammonia (1250 g), and stirred at 75~80° C. for 60 minutes. The organic phase was separated, to which was added 25% ammonia (1500 g). Then, a solution of disodium ethylenediaminetetraacetate dihydrate (EDTA) (150 g) in water (2000 g) was added. After heating at 70~80° C. for 60 minutes, the organic layer was separated. The organic layer was cooled down to 0~5° C., stirred for 2-3 hours, and vacuum filtered. The filter cake obtained was washed with toluene (2000 g), and dried under vacuum at 40~50° C., obtaining a white solid compound 6, 740 g (73.2%).

Example 5

Synthesis of the (1S,2S,3 S,4R)-3-[(1S)-1-acetylamino-2-ethyl-butyl]-4-guanidino-2-hydroxy-cyclopentyl-1-carboxylic acid crude product (9)

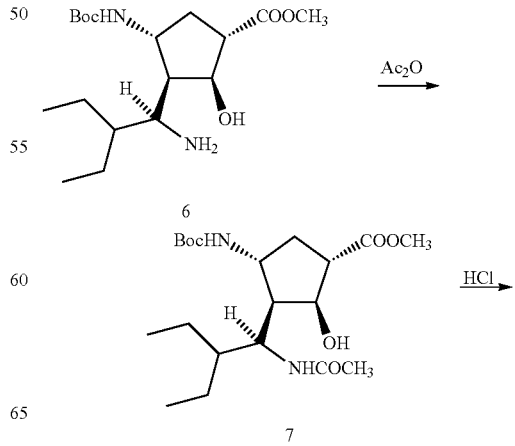

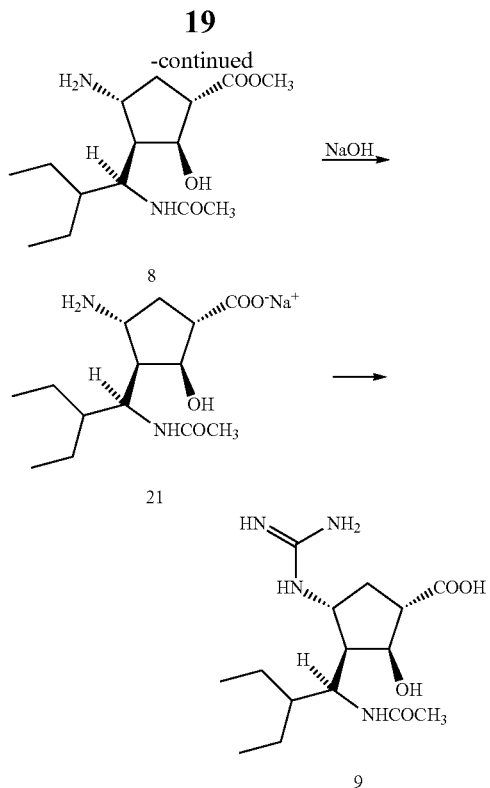

Procedures 2000 g of intermediate 6 was suspended in 10000 ml of toluene, and cooled down to 2~5° C., to which was added dropwise 680 g of acetic anhydride. After completion of the addition, the reaction mixture was stirred at room temperature for 1.5 hours. Then, 4800 ml of 10% aqueous solution of sodium carbonate was slowly added, followed by stirring for 15 minutes. The aqueous layer was discarded, and the organic layer, i.e., a toluene solution containing intermediate 7, was directly used in the subsequent step.

In an ice bath, 1900 ml of concentrated hydrochloric acid was added dropwise to the above toluene solution. After completion of the addition, the reaction mixture was stirred for 1.5 hours. After stratification, the organic layer was washed with water (1000 ml) for one time. The aqueous layers were combined, obtaining an aqueous solution containing intermediate 8, which was directly used in the subsequent step.

At 0~6° C., 2920 ml of 30% aqueous solution of sodium hydroxide was added to the above aqueous solution. After completion of the addition, the solution was further stirred for 60 minutes, obtaining an aqueous solution containing intermediate 21, which was directly used in the subsequent step.

1020 g of 1,2,4-triazole-1-formamidine hydrochloride was added to the above aqueous solution containing intermediate 21, followed by stirring for 60 minutes. Then, 30% aqueous solution of sodium hydroxide was added to adjust the pH of the reaction solution to 8.4. The reaction solution was stirred at room temperature overnight, and then stirred at 0~4° C. for 4 hours. Finally, the reaction solution was subjected to suction filtration and then dried, obtaining 1150 g of a white solid, the (1S,2S,3S,4R)-3-[(1S)-1-acetylamino-2-ethyl-butyl]-4-guanidino-2-hydroxy-cyclopentyl-1-carboxylic acid crude product, with a yield of 30%.

Example 6

Preparation of (1S,2S,3S,4R)-3-[(1S)-1-acetylamino-2-ethyl-butyl]-4-guanidino-2-hydroxy-cyclopentyl-1-carboxylic acid monohydrate 1200 g of the (1S,2S,3S,4R)-3-[(1S)-1-acetylamino-2-ethyl-butyl]-4-guanidino-2-hydroxy-cyclopentyl-1-carboxylic acid crude product was suspended in 20000 ml of water, and dissolved by heating to 90° C. After standing for a moment, 50 g of activated carbon was added to the system, followed by refluxing at 90° C. for 10 minutes, and filtering while the system was hot. After cooling down by standing to 75° C., 6000 ml of acetone was added to the filtrate. In an ice bath, the mixed solution was rapidly cooled down with stirring, so that a large amount of white powdery solid was precipitated. After cooling down to about 4° C., the mixed system was moved to a refrigerator for cold storage. After 12 hours, the mixed system was filtered, and the filter cake obtained was washed with a mixture of acetone and water. The obtained solid was naturally dried, obtaining 1100 g of a white solid product, (1S,2S,3 S,4R)-3-[(1S)-1-acetylamino-2-ethyl-butyl]-4-guanidino-2-hydroxy-cyclopentyl-1-carboxylic acid monohydrate, with a purity of 99.57% and a moisture content of 5.31%.

Example 7

Preparation of (1S,2S,3S,4R)-3-[(1S)-1-acetylamino-2-ethyl-butyl]-4-guanidino-2-hydroxy-cyclopentyl-1-carboxylic acid dihydrate 1000 g of the (1S,2S,3S,4R)-3-[(1S)-1-acetylamino-2-ethyl-butyl]-4-guanidino-2-hydroxy-cyclopentyl-1-carboxylic acid crude product was suspended in 30000 ml of water, and dissolved by heating to 90° C. After standing for a moment, 50 g of activated carbon was added to the system, followed by refluxing at 90° C. for 10 minutes, and filtering while the system was hot. After cooling down by standing to 75° C., 6000 ml of methanol was added to the filtrate. Then, the mixed solution was placed in a desiccator and sealed, and then placed in a temperature-controlled reaction tank wherein the temperature was controlled to decrease from 75° C. to −10° C. within 6 hours, so that a large amount of white powdery solid was continuously precipitated. After isothermally standing for 12 hours, the mixed system was filtered, and the filter cake obtained was washed with a mixture of methanol and water. The obtained solid was naturally dried, obtaining 880 g of a white solid product, (1S,2S,3S,4R)-3-[(1S)-1-acetylamino-2-ethyl-butyl]-4-guanidino-2-hydroxy-cyclopentyl-1-carboxylic acid dihydrate, with a purity of 99.67% and a moisture content of 9.95%.

Example 8

Preparation of (1S,2S,3S,4R)-3-[(1S)-1-acetylamino-2-ethyl-butyl]-4-guanidino-2-hydroxy-cyclopentyl-1-carboxylic acid trihydrate 1200 g of the (1S,2S,3 S,4R)-3-[(1S)-1-acetylamino-2-ethyl-butyl]-4-guanidino-2-hydroxy-cyclopentyl-1-carboxylic acid crude product was suspended in 30000 ml of water, and dissolved by heating to 90° C. After standing for a moment, 50 g of activated carbon was added to the system, followed by refluxing at 90° C. for 10 minutes, and filtering while the system was hot. After cooling down by standing to 75° C., 5000 ml of methanol was added to the filtrate. Then, the mixed solution was placed in a desiccator and sealed. After standing for several hours, a large amount of white powdery solid was precipitated. After 12 hours, the mixed system was filtered, and the filter cake obtained was washed with a mixture of methanol and water. The obtained solid was naturally dried, obtaining 1080 g of a white solid product, (1S,2S,3S,4R)-3-[(1S)-1-acetylamino-2-ethyl-butyl]-4-guanidino-2-hydroxy-cyclopentyl-1-carboxylic acid trihydrate, with a purity of 99.86% and a moisture content of 14.21%.

Example 9

Preparation of (1S,2S,3S,4R)-3-[(1S)-1-acetylamino-2-ethyl-butyl]-4-guanidino-2-hydroxy-cyclopentyl-1-carboxylic acid semihydrate 100 g of the (1S,2S,3S,4R)-3-[(1S)-1-acetylamino-2-ethyl-butyl]-4-guanidino-2-hydroxy-cyclopentyl-1-carboxylic acid crude product was suspended in 1000 ml of methanol, and dissolved by heating to 70° C. After standing for a moment, 5 g of activated carbon was added to the system, followed by refluxing at 70° C. for 10 minutes, and filtering while the system was hot. 1000 ml of water was added to the filtrate. In an ice bath, the mixed solution was rapidly cooled down with stirring, so that a large amount of white powdery solid was precipitated. After cooling down to about 4° C., the mixed system was moved to a refrigerator for cold storage. After 12 hours, the mixed system was filtered, and the filter cake obtained was washed with a mixture of methanol and water. The obtained solid was naturally dried, obtaining 84 g of a white solid product, (1S,2S,3S,4R)-3-[(1S)-1-acetylamino-2-ethyl-butyl]-4-guanidino-2-hydroxy-cyclopentyl-1-carboxylic acid semihydrate, with a purity of 99.71% and a moisture content of 2.73%.

Example 10

Preparation of (1S,2S,3S,4R)-3-[(1S)-1-acetylamino-2-ethyl-butyl]-4-guanidino-2-hydroxy-cyclopentyl-1-carboxylic acid sesquihydrate 100 g of the (1S,2S,3S,4R)-3-[(1S)-1-acetylamino-2-ethyl-butyl]-4-guanidino-2-hydroxy-cyclopentyl-1-carboxylic acid crude product was suspended in 1000 ml of acetone, and dissolved by heating to 70° C. After standing for a moment, 5 g of activated carbon was added to the system, followed by refluxing at 70° C. for 10 minutes, and filtering while the system was hot. 1200 ml of water was added to the filtrate. Then, the temperature of the mixed solution was controlled to decrease from 75° C. to 4° C. within 5 hours, so that a large amount of white powdery solid was precipitated. After cooling down to about 4° C., the mixed system was moved to a refrigerator for cold storage. After 12 hours, the mixed system was filtered, and the filter cake obtained was washed with a mixture of acetone and water. The obtained solid was naturally dried, obtaining 80 g of a white solid product, (1S,2S,3S,4R)-3-[(1S)-1-acetylamino-2-ethyl-butyl]-4-guanidino-2-hydroxy-cyclopentyl-1-carboxylic acid sesquihydrate, with a purity of 99.61% and a moisture content of 7.64%.

Example 11

Preparation of (1S,2S,3S,4R)-3-[(1S)-1-acetylamino-2-ethyl-butyl]-4-guanidino-2-hydroxy-cyclopentyl-1-carboxylic acid hexahydrate 100 g of the (1S,2S,3S,4R)-3-[(1S)-1-acetylamino-2-ethyl-butyl]-4-guanidino-2-hydroxy-cyclopentyl-1-carboxylic acid crude product was suspended in 1300 ml of water, and dissolved by heating to 100° C. After standing for a moment, 5 g of activated carbon was added to the system, followed by refluxing at 100° C. for 10 minutes, and filtering while the system was hot. The temperature of the filtrate was controlled to decrease from 75° C. to 5° C. within 1 hour, so that a large amount of white powdery solid was precipitated. After cooling down to about 4° C., the mixed system was moved to a refrigerator for cold storage. After 12 hours, the mixed system was filtered, and the filter cake obtained was washed with a mixture of methanol and water. The obtained solid was naturally dried, obtaining 78 g of a white solid product, (1S,2S,3S,4R)-3-[(1S)-1-acetylamino-2-ethyl-butyl]-4-guanidino-2-hydroxy-cyclopentyl-1-carboxylic acid hexahydrate, with a purity of 99.59% and a moisture content of 24.92%.

Example 12

Determination of solubility of (1S,2S,3S,4R)-3-[(1S)-1-acetylamino-2-ethyl-butyl]-4-guanidino-2-hydroxy-cyclopentyl-1-carboxylic acid and its hydrates According to Chinese Pharmacopoeia (2005 edition), Vol. II, General Notice 5(2), (1S,2S,3 S,4R)-3-[(1S)-1-acetylamino-2-ethyl-butyl]-4-guanidino-2-hydroxy-cyclopentyl-1-carboxylic acid and its hydrates, which had been grounded into fine powder, were weighed in a suitable amount, and put into different volumes of solvent at 25±2° C. While vigorously stirring for 30 seconds every 5 minutes, the dissolution of the powder was observed within 30 minutes. When no powder particle of (1S,2S,3S,4R)-3-[(1S)-1-acetylamino-2-ethyl-butyl]-4-guanidino-2-hydroxy-cyclopentyl-1-carboxylic acid and its hydrates was observed, it was considered that the powder was completely dissolved. The results were shown in the following table.

The determination results of solubility of (1S,2S,3S,4R)-3-[(1S)-1-acetylamino-2-ethyl-butyl]-4-guanidino-2-hydroxy-cyclopentyl-1-carboxylic acid and its hydrates

| Solvent | Samples | Solubility (g/ml) |
| --- | --- | --- |
| Water | Anhydrous | 0.08 |
|  | Monohydrate | 0.15 |
|  | Sesquihydrate | 0.03 |
|  | Dihydrate | 0.05 |
|  | Trihydrate | 0.17 |
|  | Hexahydrate | 0.11 |

Example 13

Determination of hygroscopicity of (1S,2S,3S,4R)-3-[(1S)-1-acetylamino-2-ethyl-butyl]-4-guanidino-2-hydroxy-cyclopentyl-1-carboxylic acid and its hydrates According to the method for investigating influencing factors of high humidity as specified in Guidelines for Stability Testing of Drug Substances involved in Appendix XIX C of Chinese Pharmacopoeia (2005 edition), (1S,2S,3S,4R)-3-[(1S)-1-acetylamino-2-ethyl-butyl]-4-guanidino-2-hydroxy-cyclopentyl-1-carboxylic acid and its hydrates were placed in a humidity-constant sealed vessel, under the conditions of 25° C. and a relative humidity of 90%±5%, for 10 days. At the 5$^{th}$ and 10$^{th}$ days, the products were sampled and determined in aspect of important items relating to stability investigation. Meanwhile, the weights of (1S,2S,3S,4R)-3-[(1S)-1-acetylamino-2-ethyl-butyl]-4-guanidino-2-hydroxy-cyclopentyl-1-carboxylic acid and its hydrates, before and after the experiment, were exactly weighed, to thereby investigate the hygroscopicity and deliquescence of the products. If the weight gain of a product due to moisture absorption was more than 5%, the product was further experimented according to the same method under a relative humidity of 75%±5%. If the weight gain of a product due to moisture absorption was less than 5%, and other items thereof under investigation met the relevant requirements, no more experiment was needed. The humidity-constant condition could be achieved by placing a saturated saline solution at the lower part of a sealed vessel, e.g., a desiccator, and a NaCl saturated solution (15.5-60° C., a relative humidity of 75%±1%) or a KNO$_3$ saturated solution (25° C., a relative humidity of 92.5%) may be selected according to the requirement of different relative humidity. The results were showed in the following table.

The determination results of hygroscopicity of (1S, 2S,3 S,4R)-3-[(1S)-1-cetylamino-2-ethyl-butyl]-4-guanidino-2-hydroxy-cyclopentyl-1-carboxylic acid and its hydrates

| Relative humidity | Samples | Hygroscopicity at the 5$^{th}$ day (%) | Hygroscopicity at the 10$^{th}$ day (%) | Remarks |
|---|---|---|---|---|
| 92.5% | Anhydrous | 8.38 | 13.53 | Not conform to the requirement |
| | Monohydrate | 2.83 | 3.35 | Not conform to the requirement |
| | Sesquihydrate | 4.48 | 7.33 | Not conform to the requirement |
| | Dehydrate | 2.54 | 2.98 | Conform to the requirement |
| | Trihydrate | 2.11 | 2.24 | Conform to the requirement |
| | Hexahydrate | 4.37 | 9.96 | Not conform to the requirement |
| 75% | Anhydrous | 7.23 | 12.88 | Not conform to the requirement |
| | Monohydrate | 2.41 | 2.77 | Conform to the requirement |
| | Sesquihydrate | 4.01 | 6.89 | Not conform to the requirement |
| | Dehydrate | 2.21 | 2.54 | Conform to the requirement |
| | Trihydrate | 1.68 | 1.83 | Conform to the requirement |
| | Hexahydrate | 3.86 | 6.33 | Not conform to the requirement |

Example 14

Investigation of stability of (1S,2S,3S,4R)-3-[(1S)-1-acetylamino-2-ethyl-butyl]-4-guanidino-2-hydroxy-cyclopentyl-1-carboxylic acid hydrates According to the accelerated test method as specified in Guidelines for Stability Testing of Drug Substances involved in Appendix XIX C of Chinese Pharmacopoeia (2005 edition), 3 batches of (1S,2S,3S,4R)-3-[(1S)-1-acetylamino-2-ethyl-butyl]-4-guanidino-2-hydroxy-cyclopentyl-1-carboxylic acid hydrates, in packages for sale, were placed under the conditions of a temperature of 40° C.±2° C. and a relative humidity of 75%±5% for 6 months. The device used should be capable of controlling temperature with a precise of ±2° C., and relative humidity with a precise of ±5%, and could monitor true temperature and humidity. The products were sampled respectively at the end of the 1, 2, 3 and 6 months during the test, and determined in aspect of important items relating to stability investigation. If the sample did not meet the specified quality standard as determined within 6 months under the above conditions, it should be subjected to accelerated experiment under intermediate conditions, i.e., a temperature of 30° C.±2° C. and a relative humidity of 60%±5% (NaNO$_2$ saturated solution (25-40° C., a relative humidity of 64-61.5%) might be used), for 6 months.

The investigation results of stability of (1S,2S,3S, 4R)-3-[(1S)-1-acetylamino-2-ethyl-butyl]-4-guanidino-2-hydroxy-cyclopentyl-1-carboxylic acid hydrates

| | | | Investigation items | | |
|---|---|---|---|---|---|
| Compound | Time (month) | Character | Change in weight (%) | Content (%) | Relevant substances (%) |
| Trihydrate | 0 | White solid powder | — | 99.90 | Conform to the requirement |
| | 1 | White solid powder | +0.01 | 99.95 | Conform to the requirement |
| | 2 | White solid powder | −0.02 | 99.97 | Conform to the requirement |
| | 3 | White solid powder | +0.01 | 99.96 | Conform to the requirement |
| | 6 | White solid powder | +0.01 | 99.91 | Conform to the requirement |

Example 15

Preparation of (1S,2S,3S,4R)-3-[(1S)-1-acetylamino-2-ethyl-butyl]-4-guanidino-2-hydroxy-cyclopentyl-1-carboxylic acid hydrate injection with specification of 100 mg

| Components | Weight (g) |
|---|---|
| (1S,2S,3S,4R)-3-[(1S)-1-acetylamino-2-ethyl-butyl]-4-guanidino-2-hydroxy-cyclopentyl-1-carboxylic acid trihydrate | 116.4 |
| Water for injection | 4868.6 |
| Activated carbon | 5 |
| Diluted hydrochloric acid (0.1M) | 10 |
| Total amount | 5000 |

116.4 g of (1S,2S,3S,4R)-3-[(1S)-1-acetylamino-2-ethyl-butyl]-4-guanidino-2-hydroxy-cyclopentyl-1-carboxylic acid trihydrate was dissolved in 4000 ml water for injection at 80° C. till complete dissolution. Thereafter, 5 g of activated carbon was added to the resulting solution while it was hot, to effect adsorption at 80° C. for 20 minutes. The solution was filtered, and the resulting filtrate was supplemented with water for injection to a total volume of 5000 ml. After the filtrate was cooled down to room temperature, 10 ml of 0.1 M diluted hydrochloric acid was added to adjust its pH to 3-5, followed by filtration using a filtration membrane of 0.2 μm. The resulting filtrate was filled into ampoules (1000 in total)

in an amount of 5 ml per ampoule. After completion of the filling, the ampoules were sealed, and sterilized at 115° C. for 20 minutes.

Example 16

Preparation of (1S,2S,3S,4R)-3-[(1S)-1-acetylamino-2-ethyl-butyl]-4-guanidino-2-hydroxy-cyclopentyl-1-carboxylic acid hydrate injection with specification of 50 mg

| Components | Weight (g) |
| --- | --- |
| (1S,2S,3S,4R)-3-[(1S)-1-acetylamino-2-ethyl-butyl]-4-guanidino-2-hydroxy-cyclopentyl-1-carboxylic acid trihydrate | 58.2 |
| Water for injection | 4926.8 |
| Activated carbon | 5 |
| Diluted hydrochloric acid (0.1M) | 10 |
| Total amount | 5000 |

58.2 g of (1S,2S,3S,4R)-3-[(1S)-1-acetylamino-2-ethyl-butyl]-4-guanidino-2-hydroxy-cyclopentyl-1-carboxylic acid trihydrate was dissolved in 4000 ml water for injection at 80° C. till complete dissolution. Thereafter, 5 g of activated carbon was added to the resulting solution while it was hot, to effect adsorption at 80° C. for 20 minutes. The solution was filtered, and the resulting filtrate was supplemented with water for injection to a total volume of 5000 ml. After the filtrate was cooled down to room temperature, 10 ml of 0.1 M diluted hydrochloric acid was added to adjust its pH to 3-5, followed by filtration using a filtration membrane of 0.2 μm. The resulting filtrate was filled into ampoules (1000 in total) in an amount of 5 ml per ampoule. After completion of the filling, the ampoules were sealed, and sterilized at 115° C. for 20 minutes.

Example 17

Preparation of (1S,2S,3S,4R)-3-[(1S)-1-acetylamino-2-ethyl-butyl]-4-guanidino-2-hydroxy-cyclopentyl-1-carboxylic acid hydrate injection with specification of 300 mg

| Components | Weight (g) |
| --- | --- |
| (1S,2S,3S,4R)-3-[(1S)-1-acetylamino-2-ethyl-butyl]-4-guanidino-2-hydroxy-cyclopentyl-1-carboxylic acid trihydrate | 34.9 |
| Water for injection | 9850.1 |
| Sodium chloride | 90 |
| Activated carbon | 10 |
| Sodium bisulfite | 10 |
| Sodium calciumedetate | 5 |
| Total amount | 10000 |

90 g of sodium chloride, 10 g of sodium bisulfite and 5 g of sodium calciumedetate were dissolved in 8000 ml water for injection at 80° C. till complete dissolution. Then, 34.9 g of (1S,2S,3S,4R)-3-[(1S)-1-acetylamino-2-ethyl-butyl]-4-guanidino-2-hydroxy-cyclopentyl-1-carboxylic acid trihydrate was further added therein till complete dissolution. Thereafter, 10 g of activated carbon was added to the resulting solution while it was hot, to effect adsorption at 80° C. for 20 minutes. The solution was filtered, and the resulting filtrate was supplemented with water for injection to a total volume of 10000 ml. After cooling down to room temperature, the filtrate was further filtered using a filtration membrane of 0.2 μm. The resulting filtrate was filled into ampoules (100 in total) in an amount of 100 ml per ampoule. After completion of the filling, the ampoules were sealed, and sterilized at 115° C. for 20 minutes.

Example 18

Preparation of (1S,2S,3S,4R)-3-[(1S)-1-acetylamino-2-ethyl-butyl]-4-guanidino-2-hydroxy-cyclopentyl-1-carboxylic acid hydrate injection with specification of 300 mg

| Components | Weight (g) |
| --- | --- |
| (1S,2S,3S,4R)-3-[(1S)-1-acetylamino-2-ethyl-butyl]-4-guanidino-2-hydroxy-cyclopentyl-1-carboxylic acid trihydrate | 349 |
| Water for injection | 98366 |
| Sodium chloride | 900 |
| Activated carbon | 100 |
| Diluted hydrochloric acid (1M) | 285 |
| Total amount | 100000 |

900 g of sodium chloride was dissolved in 80000 ml water for injection at 80° C. till complete dissolution. Then, 349 g of (1S,2S,3S,4R)-3-[(1S)-1-acetylamino-2-ethyl-butyl]-4-guanidino-2-hydroxy-cyclopentyl-1-carboxylic acid trihydrate was further added therein till complete dissolution. Thereafter, 100 g of activated carbon was added to the resulting solution while it was hot, to effect adsorption at 80° C. for 20 minutes. The solution was filtered to remove the activated carbon, and 285 ml of 1M diluted hydrochloric acid was added to the resulting filtrate to adjust its pH to 4-6. Then, the filtrate was supplemented with water for injection to a total volume of 100000 ml. After cooling down to room temperature, the filtrate was further filtered using a filtration membrane of 0.2 μm. The resulting filtrate was filled into ampoules (1000 in total) in an amount of 100 ml per ampoule. After completion of the filling, the ampoules were sealed, and sterilized at 115° C. for 20 minutes.

Example 19

Preparation of (1S,2S,3S,4R)-3-[(1S)-1-acetylamino-2-ethyl-butyl]-4-guanidino-2-hydroxy-cyclopentyl-1-carboxylic acid hydrate injection with specification of 500 mg

| Components | Weight (g) |
| --- | --- |
| (1S,2S,3S,4R)-3-[(1S)-1-acetylamino-2-ethyl-butyl]-4-guanidino-2-hydroxy-cyclopentyl-1-carboxylic acid trihydrate | 582 |
| Water for injection | 98133 |
| Sodium chloride | 900 |
| Activated carbon | 100 |
| Diluted hydrochloric acid (1M) | 285 |
| Total amount | 100000 |

900 g of sodium chloride was dissolved in 80000 ml water for injection at 80° C. till complete dissolution. Then, 582 g of (1S,2S,3S,4R)-3-[(1S)-1-acetylamino-2-ethyl-butyl]-4-guanidino-2-hydroxy-cyclopentyl-1-carboxylic acid trihydrate was further added therein till complete dissolution.

Thereafter, 100 g of activated carbon was added to the resulting solution while it was hot, to effect adsorption at 80° C. for 20 minutes. The solution was filtered to remove the activated carbon, and 285 ml of 1M diluted hydrochloric acid was added to the resulting filtrate to adjust its pH to 4-6. Then, the filtrate was supplemented with water for injection to a total volume of 100000 ml. After cooling down to room temperature, the filtrate was further filtered using a filtration membrane of 0.2 μm. The resulting filtrate was filled into ampoules (1000 in total) in an amount of 100 ml per ampoule. After completion of the filling, the ampoules were sealed, and sterilized at 115° C. for 20 minutes.

Example 20

Preparation of (1S,2S,3S,4R)-3-[(1S)-1-acetylamino-2-ethyl-butyl]-4-guanidino-2-hydroxy-cyclopentyl-1-carboxylic acid trihydrate powder injection preparation Formula 1

| | |
|---|---|
| (1S,2S,3S,4R)-3-[(1S)-1-acetylamino-2-ethyl-butyl]-4-guanidino-2-hydroxy-cyclopentyl-1-carboxylic acid trihydrate | 23.3 g |
| (equivalent to peramivir) | 20.0 g |
| Sodium chloride | 9.0 g |
| 0.1N diluted hydrochloric acid solution | adjusting pH to 3.5-5 |
| Water | added till 1000 ml |

200 bottles were prepared with specification of 100 mg principal agent per bottle 23.3 g of (1S,2S,3S,4R)-3-[(1S)-1-acetylamino-2-ethyl-butyl]-4-guanidino-2-hydroxy-cyclopentyl-1-carboxylic acid trihydrate and 9 g of sodium chloride were weighed in a clean room, and placed in a sterilized vessel, to which was added 500 ml of sterilized water for injection. Then, the resulting solution was adjusted with 0.1 N diluted hydrochloric acid solution to a pH of 3.5-5, and supplemented with sterilized water for injection till 1000 ml, and then adsorbed with 1 g of activated carbon. After filtration, the resulting filtrate was further filtered with a sterilizer equipped with a 0.22 μm of microfiltration membrane. The solution as finally obtained was filled into 20 ml sterilized penicillin bottles in an amount of 5 ml per bottle. The bottles were subjected to pre-freezing at −30° C.~−40° C. for 2-3 hours, sublimation drying at −36° C.~−20° C. for 9 hours, drying at 30° C. for 10-24 hours, capping, rolling-installing, and packaging, whereby the powder injection preparation was prepared.

Formula 2

The formula and the preparation method were the same as those of the general formula 1, except for that the solution as formulated was subjected to sterile drying in a large dish, followed by crushing, split charging in penicillin bottles in specified weight, capping, sealing, and packaging.

Formula 3

| | |
|---|---|
| (1S,2S,3S,4R)-3-[(1S)-1-acetylamino-2-ethyl-butyl]-4-guanidino-2-hydroxy-cyclopentyl-1-carboxylic acid trihydrate | 23.3 g |
| (equivalent to peramivir) | 20.0 g |
| mannitol | 33.6 g |
| 0.1N diluted hydrochloric acid solution | adjusting pH to 3.5-5 |
| Water | added till 1000 ml |

200 bottles were prepared with specification of 100 mg principal agent per bottle 23.3 g of (1S,2S,3S,4R)-3-[(1S)-1-acetylamino-2-ethyl-butyl]-4-guanidino-2-hydroxy-cyclopentyl-1-carboxylic acid trihydrate and 33.6 g of mannitol were weighed in a clean room, and placed in a sterilized vessel, to which was added 500 ml of sterilized water for injection. Then, the resulting solution was adjusted with 0.1 N diluted hydrochloric acid solution to a pH of 3.5-5, and supplemented with sterilized water for injection till 1000 ml, and then adsorbed with 1 g of activated carbon. After filtration, the resulting filtrate was further filtered with a sterilizer equipped with a 0.22 μm of microfiltration membrane. The solution as finally obtained was filled into 20 ml sterilized penicillin bottles in an amount of 5 ml per bottle. The bottles were subjected to pre-freezing at −30° C.~−40° C. for 2-3 hours, sublimation drying at −36° C.~−20° C. for 9 hours, drying at 30° C. for 10-24 hours, capping, rolling-installing, and packaging, whereby the powder injection preparation was prepared.

Formula 4

The formula and the preparation method were the same as those of the general formula 3, except for that the solution as formulated was subjected to sterile drying in a large dish, followed by crushing, split charging in penicillin bottles in specified weight, capping, sealing, and packaging.

Formula 5

| | |
|---|---|
| (1S,2S,3S,4R)-3-[(1S)-1-acetylamino-2-ethyl-butyl]-4-guanidino-2-hydroxy-cyclopentyl-1-carboxylic acid trihydrate | 23.3 g |
| (equivalent to peramivir) | 20.0 g |
| Sodium chloride | 9.0 g |
| 0.1N diluted acetic acid solution | adjusting pH to 3.5-5 |
| Water | added till 1000 ml |

200 bottles were prepared with specification of 100 mg principal agent per bottle 23.3 g of (1S,2S,3S,4R)-3-[(1S)-1-acetylamino-2-ethyl-butyl]-4-guanidino-2-hydroxy-cyclopentyl-1-carboxylic acid trihydrate and 9 g of sodium chloride were weighed in a clean room, and placed in a sterilized vessel, to which was added 500 ml of sterilized water for injection. Then, the resulting solution was adjusted with 0.1 N diluted acetic acid solution to a pH of 3.5-5, and supplemented with sterilized water for injection till 1000 ml, and then adsorbed with 1 g of activated carbon. After filtration, the resulting filtrate was further filtered with a sterilizer equipped with a 0.22 μm of microfiltration membrane. The solution as finally obtained was filled into 20 ml sterilized penicillin bottles in an amount of 5 ml per bottle. The bottles were subjected to pre-freezing at −30° C.~−40° C. for 2-3 hours, sublimation drying at −36° C.~−20° C. for 9 hours, drying at 30° C. for 10-24 hours, capping, rolling-installing, and packaging, whereby the powder injection preparation was prepared.

Formula 6

The formula and the preparation method were the same as those of the general formula 5, except for that the solution as formulated was subjected to sterile drying in a large dish, followed by crushing, split charging in penicillin bottles in specified weight, capping, sealing, and packaging.

Formula 7

| | |
|---|---|
| (1S,2S,3S,4R)-3-[(1S)-1-acetylamino-2-ethyl-butyl]-4-guanidino-2-hydroxy-cyclopentyl-1-carboxylic acid trihydrate | 23.3 g |

-continued

| | |
|---|---|
| (equivalent to peramivir) | 20.0 g |
| 0.1N diluted hydrochloric acid solution | adjusting pH to 3.5-5 |
| Water | added till 1000 ml |

200 bottles were prepared with specification of 100 mg principal agent per bottle 23.3 g of (1S,2S,3S,4R)-3-[(1S)-1-acetylamino-2-ethyl-butyl]-4-guanidino-2-hydroxy-cyclopentyl-1-carboxylic acid trihydrate was weighed in a clean room, and placed in a sterilized vessel, to which was added 500 ml of sterilized water for injection. Then, the resulting solution was adjusted with 0.1 N diluted acetic acid solution to a pH of 3.5-5, and supplemented with sterilized water for injection till 1000 ml, and then adsorbed with 1 g of activated carbon. After filtration, the resulting filtrate was further filtered with a sterilizer equipped with a 0.22 μm of microfiltration membrane. The solution as finally obtained was filled into 20 ml sterilized penicillin bottles in an amount of 5 ml per bottle. The bottles were subjected to pre-freezing at −30° C.~−40° C. for 2-3 hours, sublimation drying at −36° C.~−20° C. for 9 hours, drying at 30° C. for 10-24 hours, capping, rolling-installing, and packaging, whereby the powder injection preparation was prepared.

Formula 8

The formula and the preparation method were the same as those of the general formula 7, except for that the solution as formulated was subjected to sterile drying in a large dish, followed by crushing, split charging in penicillin bottles in specified weight, capping, sealing, and packaging.

Formula 9

| | |
|---|---|
| (1S,2S,3S,4R)-3-[(1S)-1-acetylamino-2-ethyl-butyl]-4-guanidino-2-hydroxy-cyclopentyl-1-carboxylic acid trihydrate | 34.95 g |
| (equivalent to peramivir) | 30.0 g |
| Sodium chloride | 9.0 g |
| 0.1N diluted hydrochloric acid solution | adjusting pH to 3.5-5 |
| Water | added till 1000 ml |

200 bottles were prepared with specification of 150 mg principal agent per bottle 34.95 g of (1S,2S,3S,4R)-3-[(1S)-1-acetylamino-2-ethyl-butyl]-4-guanidino-2-hydroxy-cyclopentyl-1-carboxylic acid trihydrate and 9 g of sodium chloride were weighed in a clean room, and placed in a sterilized vessel, to which was added 500 ml of sterilized water for injection. Then, the resulting solution was adjusted with 0.1 N diluted hydrochloric acid solution to a pH of 3.5-5, and supplemented with sterilized water for injection till 1000 ml, and then adsorbed with 1 g of activated carbon. After filtration, the resulting filtrate was further filtered with a sterilizer equipped with a 0.22 μm of microfiltration membrane. The solution as finally obtained was filled into 20 ml sterilized penicillin bottles in an amount of 5 ml per bottle. The bottles were subjected to pre-freezing at −30° C.~−40° C. for 2-3 hours, sublimation drying at −36° C.~−20° C. for 9 hours, drying at 30° C. for 10-24 hours, capping, rolling-installing, and packaging, whereby the powder injection preparation was prepared.

Formula 10

The formula and the preparation method were the same as those of the general formula 9, except for that the solution as formulated was subjected to sterile drying in a large dish, followed by crushing, split charging in penicillin bottles in specified weight, capping, sealing, and packaging.

Formula 11

| | |
|---|---|
| (1S,2S,3S,4R)-3-[(1S)-1-acetylamino-2-ethyl-butyl]-4-guanidino-2-hydroxy-cyclopentyl-1-carboxylic acid trihydrate | 34.95 g |
| (equivalent to peramivir) | 30.0 g |
| Sodium chloride | 9.0 g |
| 0.1N diluted hydrochloric acid solution | adjusting pH to 3.5-5 |
| Water | added till 1000 ml |

100 bottles were prepared with specification of 300 mg principal agent per bottle 34.95 g of (1S,2S,3S,4R)-3-[(1S)-1-acetylamino-2-ethyl-butyl]-4-guanidino-2-hydroxy-cyclopentyl-1-carboxylic acid trihydrate and 9 g of sodium chloride were weighed in a clean room, and placed in a sterilized vessel, to which was added 500 ml of sterilized water for injection. Then, the resulting solution was adjusted with 0.1 N diluted hydrochloric acid solution to a pH of 3.5-5, and supplemented with sterilized water for injection till 1000 ml, and then adsorbed with 1 g of activated carbon. After filtration, the resulting filtrate was further filtered with a sterilizer equipped with a 0.22 μm of microfiltration membrane. The solution as finally obtained was filled into 50 ml sterilized penicillin bottles in an amount of 10 ml per bottle. The bottles were subjected to pre-freezing at −30° C.~−40° C. for 2-3 hours, sublimation drying at −36° C.~−20° C. for 9 hours, drying at 30° C. for 10-24 hours, capping, rolling-installing, and packaging, whereby the powder injection preparation was prepared.

Example 20

Investigation of dissolution behavior of (1S,2S,3S,4R)-3-[(1S)-1-acetylamino-2-ethyl-butyl]-4-guanidino-2-hydroxy-cyclopentyl-1-carboxylic acid hydrate in water A pre-test was carried out with the specification of 100 ml:300 mg wherein the raw material is the (1S,2S,3S,4R)-3-[(1S)-1-acetylamino-2-ethyl-butyl]-4-guanidino-2-hydroxy-cyclopentyl-1-carboxylic acid trihydrate and the dissolution conditions were as follows:

(1) water for injection (room temperature)

(2) water for injection (80° C.)

(3) water for injection (room temperature, adjusted to be acidic with hydrochloric acid)

(4) water for injection (adjusted to be basic with disodium hydrogen phosphate)

Results:

Under the condition (1), the compound was slowly dissolved while using water for injection in its total amount, with stirring or ultrasonic dissolution for a relatively long period of time. Under the condition (2), the compound was rapidly dissolved while using water for injection in a relatively little volume; considering the fact that water for injection is generally circulated at 80° C. during scale production, this condition is the preferred condition for the convenience of production. Under the condition (3), the compound was relatively easily dissolved, and as compared with the case under the condition (4), the compound was more easily dissolved under acidic condition, which could serve as a basis for the adjustment of pH value.

Example 21

Influence of different acidic conditions on the stability of (1S,2S,3S,4R)-3-[(1S)-1-acetylamino-2-ethyl-butyl]-4-guanidino-2-hydroxy-cyclopentyl-1-carboxylic acid hydrate 349 mg of (1S,2S,3S,4R)-3-[(1S)-1-acetylamino-2-ethyl-butyl]-4-guanidino-2-hydroxy-cyclopentyl-1-carboxylic acid trihydrate and 900 mg of sodium chloride were dissolved with water for injection at 80° C. according to the dissolution behavior of the trihydrate, and adjusted with hydrochloric acid to different pH values. The resulting solutions were high pressure steam sterilized at 115° C. for 30 minutes. Then, the solutions were sampled for the determination of change in pH value and change in amount of relevant substances. The results were listed as follows:

Table of pH determination

| No. of solution | Appearance | pH value Before sterilization | pH value After sterilization | Amount (relevant substances) Before sterilization | Amount (relevant substances) After sterilization | After 10 days at 60° C. |
|---|---|---|---|---|---|---|
| 1 | Colorless transparent liquid | 4.00 | 4.08 | 98.58 (0.11) | 97.8 (0.17) (2 impure peaks) | 101.20 (0.10) |
| 2 | Colorless transparent liquid | 4.53 | 4.50 | 102.90 (0.11) | 99.3 (0.10) | 96.1 (0.09) |
| 3 | Colorless transparent liquid | 5.02 | 5.02 | 101.1 (0.10) | 101.7 (0.10) | 100.4 (0.10) |
| 4 | Colorless transparent liquid | 5.40 | 5.40 | 104.3 (0.29) (2 impure peaks) | 101.7 (0.10) | 102.8 (0.09) |
| 5 | Colorless transparent liquid | 6.08 | 6.04 | 103.8 (0.11) | 102.5 (0.10) | 104.0 (0.10) |
| 6 | Colorless transparent liquid | 6.56 | 6.30 | 104.2 (0.10) | –(0.10) | 104.4 (0.39) (5 impure peaks) |
| 7 | Colorless transparent liquid | 6.95 | 6.40 | 102.90 (0.10) | 95.7 (0.10) | 93.43 (0.11) |
| 8 | Colorless transparent liquid | 7.53 | 6.72 | 104.1 (0.10) | 98.8 (0.09) | 103.9 (0.16) (3 impure peaks) |
| 9 | Colorless transparent liquid | 7.93 | 7.09 | 104.1 (0.20) (3 impure peaks) | 94.3 (0.10) | 102.73 (0.27) |

Notes:
the data inside the parentheses was the amount of relevant substances, and calculated by normalization method. The data outside the parentheses was the amount of the trihydrate.

The results showed that: when the pH value exceeded 6.5, it was reduced after sterilization, and the extent of reduction was increased as the pH value increased, which indicated that the pH value of the system could be changed by high temperature when said pH value was high. With respect to the change in amount, when the pH value exceeded 7.0, the amount after sterilization was obviously reduced, and continuously reduced after 10 days at 60° C.; when the pH value was 4.5, the amount also tended to reduce after 10 days at 60° C. This indicated that either too high or too low pH value exerted an adverse influence on the stability of the system. The analysis on relevant substances indicated that, as calculated by normalization method, the amount of the relevant substances had no obvious change, but the number of impure peaks exhibited that the number of relevant substances tended to increase as the pH value became more basic. Therefore, the compound tended to be stable under acidic conditions. The optimum pH value was within the range of 4.5-6.5.

Example 22

Study on Conditions of Adsorption and Sterilization with Activated Carbon

The change in amount before and after adsorption with activated carbon, used in amounts of 0.05%, 0.1% and 0.2% respectively, was investigated. The results showed that the adsorption amount was increased as the amount of activated carbon increased, and the adsorption amount was about 2% when the amount of activated carbon was 0.1%. In order to assure the quality of the product, activated carbon was used in an amount of 0.1%. Sterilization was performed under two conventional conditions, i.e., 115° C., 30 minutes and 121° C., 20 minutes, respectively. The results showed that the amount was somewhat reduced under the condition of 121° C., 20 minutes, and the use of a conventional sterilization method under the condition of 115° C., 30 minutes just could result in F0>8.

Example 23

Study on optimizing the formula of pharmaceutical composition for parenteral administration comprising the (1S,2S,3S,4R)-3-[(1S)-1-acetylamino-2-ethyl-butyl]-4-guanidino-2-hydroxy-cyclopentyl-1-carboxylic acid hydrate According to the basic formula:

| | |
|---|---|
| Trihydrate | 349 mg |
| Sodium chloride | 0.9 g |
| Water for injection | 100 ml | three samples were prepared as follows: by adjusting the pH value with diluted hydrochloric acid, the sample prepared with pH=5.0 was marked as SY1, the sample prepared with pH=6.0 was marked as SY2, and the sample prepared with pH=6.5 was marked as SY3. The samples prepared were subjected to high temperature, illumination experiments, and 40° C. accelerated experiment.

According to the basic formula:

| | |
|---|---|
| Trihydrate | 116.4 mg |
| Water for injection | 5 ml | three samples were prepared as follows: by adjusting the pH value with hydrochloric acid to 5.04, the sample prepared was marked as XZ1; by adding 0.05% thiourea and adjusting the pH value with ammonia to 6.98, the sample prepared was marked as XZ2; by directly dissolving trihydrate in water for injection without the addition of any adjuvant and pH adjusting agent, the sample prepared was marked as XZ3. The samples prepared were subjected to high temperature, illumination experiments, and 40° C. accelerated experiment.

The results were showed in the following table:

| Sample | Before sterilization | 0 d | Illumination 5 d | Illumination 10 d | 60° C. 5 d | 60° C. 10 d | 40° C. 10 d |
|---|---|---|---|---|---|---|---|
| pH value | | | | | | | |
| SY1 | 5.07 | 5.06 | 5.08 | 5.10 | 5.08 | 5.10 | 5.06 |
| SY2 | 5.95 | 5.99 | 6.03 | 6.01 | 6.04 | 6.07 | 6.03 |
| SY3 | 6.20 | 6.39 | 6.21 | 6.22 | 6.29 | 6.31 | 6.29 |
| XZ1 | 5.04 | 5.03 | 5.05 | 5.03 | 5.06 | 5.05 | 5.05 |
| XZ2 | 6.98 | 6.88 | 6.88 | 6.90 | 6.91 | 6.86 | 6.89 |
| XZ3 | 7.22 | 6.98 | 6.99 | 6.97 | 6.96 | 6.95 | 6.93 |
| Amount (%) | | | | | | | |
| SY1 | 101.2 | 100.5 | 99.5 | 100.2 | 99.3 | 100.9 | 100.2 |
| SY2 | 100.8 | 99.6 | 99.0 | 99.5 | 100.1 | 99.2 | 99.1 |
| SY3 | 102.5 | 99.8 | 99.1 | 98.2 | 99.1 | 98.2 | 99.6 |
| XZ1 | 98.5 | 97.8 | 98.0 | 98.2 | 99.6 | 100.9 | 100.2 |
| XZ2 | 100.0 | 98.6 | 99.7 | 98.5 | 97.1 | 98.0 | 99.8 |
| XZ3 | 101.1 | 97.5 | 98.1 | 97.8 | 98.1 | 98.3 | 99.9 |
| Relevant substances (%) | | | | | | | |
| SY1 | 0.10 | 0.11 | 0.09 | 0.11 | 0.12 | 0.09 | 0.10 |
| SY2 | 0.09 | 0.13 | 0.12 | 0.18 | 0.13 | 0.10 | 0.12 |
| SY3 | 0.13 | 0.15 | 0.17 | 0.20 | 0.15 | 0.18 | 0.11 |
| XZ1 | 0.13 | 0.12 | 0.11 | 0.10 | 0.12 | 0.16 | 0.11 |
| XZ2 | 0.12 | 0.14 | 0.15 | 0.18 | 0.09 | 0.14 | 0.10 |
| XZ3 | 0.11 | 0.18 | 0.20 | 0.11 | 0.19 | 0.27 | 0.18 |

Example 24

Determination of inhibitory activity of (1S,2S,3S,4R)-3-[(1S)-1-acetylamino-2-ethyl-butyl]-4-guanidino-2-hydroxy-cyclopentyl-1-carboxylic acid hydrate against influenza A virus neuraminidase Using 4-MUNANA as a substrate, the activity of influenza virus neuraminidase and the inhibitory activity of the candidate compound against neuraminidase were assayed by fluorimetry. A stock solution of first generation viruses was cultivated in MDCK cells, and diluted with a neuraminidase assay buffer (NA assay buffer: 32.5 MES, 4 mM $CaCl_2$, pH6.5) in a ratio of 1:2. 50 µl of the resulting virus diluted solution was mixed with equal volume of 4-MUNANA (200 mM in NA assay buffer) in a black 96-well plate (Costar), and incubated at 37° C. for 1 hour, and then 2 times by volume of a stop buffer (25% ethanol, 0.1M glycine, pH 10.7) was added to stop the reaction. The fluorescence intensities at Excitation: 360 nM and Emission: 460 nM were assayed (PolarSTAR Optima, BMG Labtech, Germany). A scatter diagram of net value of fluorescence unit vs. virus concentration was plotted, and two virus concentrations with activity lying in the middle of the linear part of the scatter diagram were selected and used for the assay of the inhibitory activity of the compound. Solutions of (1S,2S,3 S,4R)-3-[(1S)-1-acetylamino-2-ethyl-butyl]-4-guanidino-2-hydroxy-cyclopentyl-1-carboxylic acid trihydrate having concentrations of 0.01, 0.1, 1, 10, 100 pMol were respectively formulated using sterile deionized water. 25 µl of the respective solutions were mixed with equal amount of viruses (in a concentration two times of that selected in the activity assay) that had been diluted with 2×NA assay buffer, followed by acting at room temperature for 30 minutes, and then 50 µl of 4-MUNANA (200 mM in NA assay buffer) was added, followed by incubating at 37° C. for 1 hour, and finally the fluorescence intensity was assayed as above described. Each of the concentrations of the candidate compound was provided in two parallel holes, the blank control was provided in 4 parallel holes, which only included 4-MUNANA and the stop buffer, and the virus control was provided in 4 parallel holes, which contained the candidate compound in a concentration of zero. The inhibitory rate IR (%) was calculated according to the following equation:

IR (%)=[1−(FU−FUB)÷(FUC−FUB)]×100

FU: average value of fluorescence unit in the candidate compound group;

FUB: average value of fluorescence unit in the blank control group;

FUC: average value of fluorescence unit in the virus control group.

A scatter diagram of IR (%) vs. concentration of compound was plotted, and $IC_{50}$ was calculated by logarithmic regression analysis. The regression curves obtained from the assay results of different virus concentrations should preferably overlap, with similar $IC_{50}$ values. The results were listed as follows:

| Inhibitory activity against influenza A virus (H3N2) neuraminidase | | | | | | | | |
|---|---|---|---|---|---|---|---|---|
| Con. (nM) | 100 | 10 | 1 | 0.1 | 0.01 | Ln ($IC_{50}$) | $IC_{50}$ | Average $IC_{50}$ |
| NA 1/40 | 100.43 | 99.25 | 60.99 | 13.23 | 0.63 | −0.39549 | 0.673353 | 0.542104 |
| NA 1/80 | 99.89 | 98.80 | 63.20 | 24.04 | 12.33 | −0.88951 | 0.410856 | |

*NA 1/40, NA 1/80 refer to two virus concentrations used in the experiment.

Example 25

Determination of inhibitory activity of (1S,2S,3S,4R)-3-[(1S)-1-acetylamino-2-ethyl-butyl]-4-guanidino-2-hydroxy-cyclopentyl-1-carboxylic acid hydrate against influenza B virus neuraminidase The inhibitory activity of (1S,2S,3S,4R)-3-[(1S)-1-acetylamino-2-ethyl-butyl]-4-guanidino-2-hydroxy-cyclopentyl-1-carboxylic acid trihydrate against influenza B virus neuraminidase was determined according to the method described in Example 24, wherein influenza B virus (B/Jing Fang/76/98) neuraminidase was used in place of influenza A virus neuraminidase. The results were listed as follows:

| Inhibitory activity against influenza B virus (B/Jing Fang/76/98) neuraminidase | | | | | | | | |
|---|---|---|---|---|---|---|---|---|
| Con. (nM) | 100 | 10 | 1 | 0.1 | 0.01 | Ln ($IC_{50}$) | $IC_{50}$ | Average $IC_{50}$ |
| NA 1/20 | 97.78 | 82.01 | 39.11 | 15.31 | 8.81 | 0.131306 | 1.140317 | 1.0691996 |
| NA 1/40 | 96.71 | 81.45 | 44.84 | 19.17 | 7.92 | −0.00192 | 0.998082 | |

*NA 1/20, NA 1/40 refer to two virus concentrations used in the experiment.

Example 26

Experiment of anti-influenza activity of (1S,2S,3S,4R)-3-[(1S)-1-acetylamino-2-ethyl-butyl]-4-guanidino-2-hydroxy-cyclopentyl-1-carboxylic acid hydrate A solution was prepared by including 500 pfu (plaque forming unit) of mice-compliance influenza virus strain FM1 (H1N1) in 50 μl phosphate buffer (containing 0.42% bovine serum albumin), and then dropped into nasal cavity of mice (BALB/C, female, aged 5-6 weeks, weighted 20 g) to infect them with an infective dose of $23.7LD_{50}$. The compound of the invention was suspended in physiological saline, and was administered in doses of 2.5 mg/kg, 5 mg/kg, 10 mg/kg, 20 mg/kg to the mice by intraperitoneal injection for 5 times, i.e., 1 hour, and 2, 3, 4, 5 days after the viral infection, respectively. The assay was performed by 10 mice. The result was expressed by the ratio of the number of survival mice the $14^{th}$ day after the viral infection to the number of the mice in assay. Meanwhile, anhydrous (1S,2S,3S,4R)-3-[(1S)-1-acetylamino-2-ethyl-butyl]-4-guanidino-2-hydroxy-cyclopentyl-1-carboxylic acid was used as a control compound.

| Dose | Reagent | Survival number | Survival rate |
|---|---|---|---|
| blank control | physiological saline | 10/10 | 100% |
| virus control | physiological saline | 0/10 | 0% |
| 2.5 mg/kg | trihydrate | 6/10 | 60% |
| | anhydrous | 5/10 | 50% |

-continued

| Dose | Reagent | Survival number | Survival rate |
|---|---|---|---|
| 5.0 mg/kg | trihydrate | 7/10 | 70% |
| | anhydrous | 7/10 | 70% |
| 10 mg/kg | trihydrate | 8/10 | 80% |
| | anhydrous | 7/10 | 70% |
| 20 mg/kg | trihydrate | 9/10 | 90% |
| | anhydrous | 9/10 | 90% |

What is claimed is:

1. A method for preparing a compound of the general formula (I),

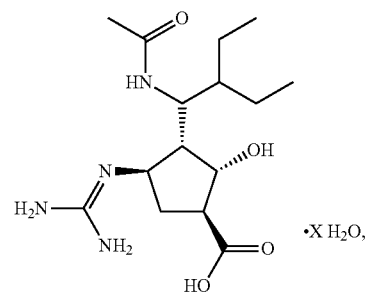

wherein X is 2.0 or 3.0, comprising the steps of:
suspending (1S,2S,3S,4R)-3-[(1S)-1-acetylamino-2-ethyl-butyl]-4-guanidino-2-hydroxy-cyclopentyl-1-carboxylic acid crude product in water and dissolving by heating to 50-90° C. to afford a first solution;
allowing the first solution to stand for a moment and then adding activated carbon to the first solution;
refluxing the first solution by heating for 10 minutes and filtering while the first solution is hot to remove the activated carbon;
cooling the first solution to 35-75° C. and then adding an organic solvent to the first solution to afford a second solution;
adding a crystal seed of the compound of the general formula (I) to the second solution;
placing the second solution in a sealed vessel, allowing the second solution to stand, and cooling the second solution at a suitable cooling rate to precipitate the compound of the general formula (I) as a crystal product,
and then filtering and collecting the compound of the general formula (I).

2. The method according to claim 1, wherein the organic solvent is one selected from the group consisting of methanol, ethanol, n-butanol, acetone and acetonitrile or a mixture thereof.

3. The method according to claim 2, wherein the organic solvent is one selected from the group consisting of methanol and acetone.

4. The method according to claim 1, wherein the second solution comprises water and the organic solvent in a ratio from 1:5 to 100:1.

5. The method according to claim 1, wherein the cooling rate is from 0.1° C./min to 5° C./min.

6. A method for preparing a compound of the general formula (I),

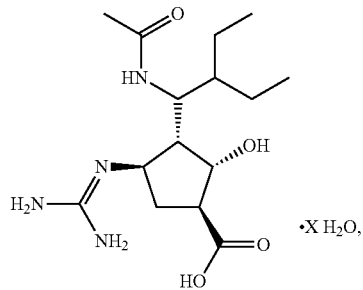

wherein X is 2.0 or 3.0,
comprising the steps of:
dissolving (1S,2S,3S,4R)-3-[(1S)-1-acetylamino-2-ethyl-butyl]-4-guanidino-2-hydroxy-cyclopentyl-1-carboxylic acid crude product in water to afford a first solution;
adding an organic solvent to the first solution to afford a second solution;
cooling the second solution at a suitable cooling rate to precipitate the compound of the general formula (I) as a crystal product; and
separating the crystal product from the second solution to isolate the compound of the general formula (I).

7. The method according to claim 6, wherein the organic solvent is one selected from the group consisting of methanol, ethanol, n-butanol, acetone and acetonitrile or a mixture thereof.

8. The method according to claim 7, wherein the organic solvent is one selected from the group consisting of methanol and acetone.

9. The method according to claim 6, wherein the second solution comprises water and the organic solvent in a ratio from 1:5 to 100:1.

10. The method according to claim 6, wherein the cooling rate is from 0.1° C./min to 5° C./min.

11. The method according to claim 6, wherein said dissolving (1S,2S,3 S,4R)-3-[(1S)-1-acetylamino-2-ethyl-butyl]-4-guanidino-2-hydroxy-cyclopentyl-1-carboxylic acid crude product in water to afford a first solution comprises:
suspending (1S,2S,3 S,4R)-3-[(1S)-1-acetylamino-2-ethyl-butyl]-4-guanidino-2-hydroxy-cyclopentyl-1-carboxylic acid crude product in water to afford a suspension; and
heating the suspension to 50-90° C. to dissolve the (1S,2S,3S,4R)-3-[(1S)-1-acetylamino-2-ethyl-butyl]-4-guanidino-2-hydroxy-cyclopentyl-1-carboxylic acid crude product to afford the first solution.

12. The method according to claim 6, further comprising, before said adding an organic solvent to the first solution to afford a second solution:
adding activated carbon to the first solution;
heating the first solution to reflux;
filtering the first solution; and
cooling the first solution to 35-75° C.

13. The method according to claim 6, further comprising, before said cooling the second solution at a suitable cooling rate to precipitate the compound of the general formula (I) as a crystal product, placing the second solution in a sealed vessel.

14. The method according to claim 6, further comprising, before said cooling the second solution at a suitable cooling rate to precipitate the compound of the general formula (I) as a crystal product, adding a crystal seed of the compound of the general formula (I) to the second solution.

15. The method according to claim 6, further comprising, before said adding an organic solvent to the first solution to afford a second solution, adjusting the temperature of the first solution to 35-75° C.

16. The method according to claim 15, wherein the cooling rate is from 0.1° C./min to 5° C./min.

17. The method according to claim 6, wherein X is 2.0.

18. The method according to claim 6, wherein X is 3.0.

19. The method according to claim 6, wherein said cooling the second solution at a suitable cooling rate comprises:
cooling the second solution from 75° C. to −10° C. within 6 hours; and
allowing the second solution to stand at −10° C. for 12 hours.

20. The method according to claim 6, wherein said cooling the second solution at a suitable cooling rate comprises allowing the second solution to stand for 12 hours.

* * * * *